(12) United States Patent
Scandurra et al.

(10) Patent No.: US 10,751,519 B2
(45) Date of Patent: *Aug. 25, 2020

(54) SYSTEM AND METHOD FOR REDUCING PULSATILE PRESSURE

(71) Applicant: Aria CV, Inc, St. Paul, MN (US)

(72) Inventors: John Scandurra, St. Paul, MN (US); Karl Vollmers, Minneapolis, MN (US)

(73) Assignee: Aria CV, Inc., St. Paul, MN (US)

( * ) Notice: Subject to any disclaimer, the term of this patent is extended or adjusted under 35 U.S.C. 154(b) by 139 days.

This patent is subject to a terminal disclaimer.

(21) Appl. No.: 14/955,109

(22) Filed: Dec. 1, 2015

(65) Prior Publication Data

US 2016/0082169 A1    Mar. 24, 2016

Related U.S. Application Data

(63) Continuation of application No. 14/253,127, filed on Apr. 15, 2014, now Pat. No. 9,333,328, which is a (Continued)

(51) Int. Cl.
*A61M 29/02* (2006.01)
*A61M 1/10* (2006.01)
(Continued)

(52) U.S. Cl.
CPC .......... *A61M 29/02* (2013.01); *A61M 1/1032* (2014.02); *A61M 1/1044* (2014.02);
(Continued)

(58) Field of Classification Search
CPC .............. A61M 1/1074; A61M 1/1044; A61M 1/1032; A61M 1/125; A61M 25/1018;
(Continued)

(56) References Cited

U.S. PATENT DOCUMENTS 3,275,001 A    9/1966    Rosecrans
3,634,924 A    1/1972    Blake et al.
(Continued)

FOREIGN PATENT DOCUMENTS

CN    102657910    9/2012
CN    103260547 A    8/2013
(Continued)

OTHER PUBLICATIONS

PCT International Search Report in corresponding application PCT/US2011/061815, dated Mar. 8, 2012, 3 pages.
(Continued)

*Primary Examiner* — Erich G Herbermann
(74) *Attorney, Agent, or Firm* — Eversheds Sutherland (US) LLP; Christopher C. Bolten; Nicola A. Pisano

(57) ABSTRACT

A device for reducing pressure within a lumen includes a reservoir structured for holding a fluid therein, an injection port in fluid communication with the reservoir, a compliant body structured to expand and contract upon changes in pressure, and a conduit extending between and fluidly coupling the reservoir and the compliant body. The fluid may be a compressible or a noncompressible fluid.

42 Claims, 15 Drawing Sheets

Related U.S. Application Data continuation of application No. 13/884,169, filed as application No. PCT/US2011/061815 on Nov. 22, 2011, now Pat. No. 9,017,359.

(60) Provisional application No. 61/416,187, filed on Nov. 22, 2010.

(51) Int. Cl.
  *A61M 25/04* (2006.01)
  *A61M 1/12* (2006.01)
  *A61M 25/10* (2013.01)

(52) U.S. Cl.
  CPC .......... *A61M 1/1072* (2013.01); *A61M 25/04* (2013.01); *A61M 1/1005* (2014.02); *A61M 1/106* (2013.01); *A61M 1/107* (2013.01); *A61M 1/1008* (2014.02); *A61M 1/1074* (2014.02); *A61M 1/1086* (2013.01); *A61M 1/12* (2013.01); *A61M 1/125* (2014.02); *A61M 25/1018* (2013.01); *A61M 25/10184* (2013.11); *A61M 2205/33* (2013.01); *A61M 2205/3303* (2013.01)

(58) Field of Classification Search
  CPC .............. A61M 25/0169; A61M 25/04; A61M 2015/1045; A61M 2015/09125; A61F 2/954
  USPC .............. 606/192–195, 200; 604/506, 96.01; 600/17
  See application file for complete search history.

(56) References Cited

U.S. PATENT DOCUMENTS

| | | |
|---|---|---|
| 3,818,903 A | 6/1974 | Bleecker |
| 4,422,447 A * | 12/1983 | Schiff .................. A61M 25/10 600/18 |
| 4,793,351 A * | 12/1988 | Landman .............. A61M 25/10 604/915 |
| 4,902,273 A | 2/1990 | Choy et al. |
| 4,938,766 A | 7/1990 | Jarvik |
| 4,955,905 A * | 9/1990 | Reed ....................... A61B 90/06 604/97.02 |
| 5,002,531 A | 3/1991 | Bonzel |
| 5,112,303 A | 5/1992 | Pudenz et al. |
| 5,222,980 A | 6/1993 | Gealow |
| 5,409,444 A * | 4/1995 | Kensey ............ A61B 17/12109 600/16 |
| 5,496,311 A | 3/1996 | Abele et al. |
| 5,713,867 A | 2/1998 | Morris |
| 5,769,821 A | 6/1998 | Abrahamson et al. |
| 5,795,325 A | 8/1998 | Valley et al. |
| 5,814,016 A | 9/1998 | Valley et al. |
| 5,820,542 A | 10/1998 | Dobak et al. |
| 5,833,655 A | 11/1998 | Freed et al. |
| 6,017,324 A | 1/2000 | Tu et al. |
| 6,030,336 A * | 2/2000 | Franchi ................. A61M 1/106 600/16 |
| 6,053,891 A | 4/2000 | Decampli |
| 6,136,025 A | 10/2000 | Barbut et al. |
| 6,210,318 B1 * | 4/2001 | Lederman ........... A61M 1/1072 600/18 |
| 6,261,304 B1 | 7/2001 | Hall et al. |
| 6,461,367 B1 | 10/2002 | Kirsch et al. |
| 6,558,349 B1 | 5/2003 | Kirkman |
| 6,559,349 B1 | 5/2003 | Slaugh et al. |
| 6,576,007 B2 | 6/2003 | Dehdashtian et al. |
| 6,579,224 B1 | 6/2003 | Burton et al. |
| 6,682,473 B1 | 1/2004 | Matsuura et al. |
| 7,044,967 B1 | 5/2006 | Solem et al. |
| 7,074,178 B2 | 7/2006 | Connors et al. |
| 7,468,050 B1 | 12/2008 | Kantrowitz |
| 7,540,876 B2 | 6/2009 | Conners et al. |
| 7,766,814 B2 | 8/2010 | Walsh |
| 7,811,249 B2 | 10/2010 | Saab |
| 7,928,367 B2 | 4/2011 | Hirota et al. |
| 8,016,740 B2 | 9/2011 | Connors et al. |
| 8,092,521 B2 | 1/2012 | Figulla et al. |
| 8,116,883 B2 | 2/2012 | Williams et al. |
| 8,206,378 B1 | 6/2012 | Kalpin et al. |
| 8,585,572 B2 | 11/2013 | Mehmanesh |
| 8,747,386 B2 | 6/2014 | Rykhus et al. |
| 8,876,850 B1 | 11/2014 | Vollmers et al. |
| 8,882,653 B2 | 11/2014 | Gillespie, Jr. et al. |
| 8,956,379 B2 | 2/2015 | Luciano et al. |
| 9,017,359 B2 | 4/2015 | Scandurra et al. |
| 9,039,725 B1 | 5/2015 | Vollmers et al. |
| 9,107,992 B2 | 8/2015 | Kushwaha et al. |
| 9,242,082 B2 | 1/2016 | Vollmers et al. |
| 9,333,328 B2 | 5/2016 | Scandurra et al. |
| 9,610,391 B2 | 4/2017 | Vollmers et al. |
| 9,801,989 B2 | 10/2017 | Vollmers et al. |
| 9,987,153 B2 | 6/2018 | Scandurra et al. |
| 10,327,880 B2 | 6/2019 | Connors et al. |
| 10,350,397 B2 | 7/2019 | Scandurra et al. |
| 10,376,681 B2 | 8/2019 | Bak-Boychuk et al. |
| 10,617,538 B2 | 4/2020 | Scandurra et al. |
| 2001/0023332 A1 | 9/2001 | Hahnen |
| 2003/0055465 A1 | 3/2003 | Ben-Haim et al. |
| 2003/0208259 A1 | 11/2003 | Penhasi |
| 2004/0093007 A1 | 5/2004 | Sussman et al. |
| 2004/0106971 A1 | 6/2004 | Schwartz et al. |
| 2004/0111006 A1 | 6/2004 | Alferness et al. |
| 2004/0143319 A1 | 7/2004 | Schwartz et al. |
| 2004/0210304 A1 | 10/2004 | Seguin et al. |
| 2005/0015107 A1 | 1/2005 | O'Brien |
| 2005/0059965 A1 | 3/2005 | Eberl et al. |
| 2005/0070938 A1 | 3/2005 | Copa et al. |
| 2005/0131451 A1 | 6/2005 | Kleshinski et al. |
| 2005/0267596 A1 | 12/2005 | Chen et al. |
| 2006/0085028 A1 | 4/2006 | Boock |
| 2006/0106450 A1 | 5/2006 | Ben Muvhar |
| 2006/0129083 A1 | 6/2006 | Brenneman et al. |
| 2006/0135962 A1 | 6/2006 | Kick et al. |
| 2006/0155310 A1 | 7/2006 | Binmoeller |
| 2006/0241745 A1 | 10/2006 | Solem |
| 2006/0253095 A1 | 11/2006 | Stull |
| 2007/0142819 A1 * | 6/2007 | El-Nounou ........ A61M 25/1011 604/509 |
| 2007/0156013 A1 | 7/2007 | Birk |
| 2007/0156167 A1 | 7/2007 | Connors et al. |
| 2008/0114338 A1 | 5/2008 | Kumar |
| 2008/0132750 A1 | 6/2008 | Miller |
| 2008/0147181 A1 | 6/2008 | Ghione et al. |
| 2008/0194905 A1 * | 8/2008 | Walsh ....................... A61F 2/06 600/17 |
| 2008/0195174 A1 | 8/2008 | Walker et al. |
| 2008/0243093 A1 | 10/2008 | Kalpin et al. |
| 2008/0312679 A1 | 12/2008 | Hardert et al. |
| 2009/0143837 A1 | 6/2009 | Rossing et al. |
| 2009/0222083 A1 | 9/2009 | Nguyen et al. |
| 2009/0240277 A1 | 9/2009 | Connors et al. |
| 2009/0294031 A1 | 12/2009 | Pepper et al. |
| 2010/0042070 A1 | 2/2010 | Gill et al. |
| 2010/0099945 A1 | 4/2010 | Birk et al. |
| 2010/0185049 A1 | 7/2010 | Birk et al. |
| 2010/0197994 A1 | 8/2010 | Mehmanesh |
| 2010/0204590 A1 | 8/2010 | Hatib et al. |
| 2010/0274221 A1 | 10/2010 | Sigg et al. |
| 2010/0324472 A1 | 12/2010 | Wulfman |
| 2010/0331767 A1 | 12/2010 | Frankowski et al. |
| 2011/0124951 A1 | 5/2011 | Walsh |
| 2011/0137210 A1 | 6/2011 | Johnson |
| 2011/0137428 A1 * | 6/2011 | Terliuc .................. A61F 5/0089 623/23.64 |
| 2012/0053514 A1 | 3/2012 | Robinson et al. |
| 2012/0083646 A1 * | 4/2012 | Benson ................ A61N 5/1015 600/3 |
| 2012/0172654 A1 | 7/2012 | Bates |
| 2013/0079871 A1 | 3/2013 | Scandurra et al. |
| 2013/0165964 A1 | 6/2013 | Vollmers et al. |

(56) References Cited

U.S. PATENT DOCUMENTS

| | | |
|---|---|---|
| 2013/0245665 A1 | 9/2013 | Scandurra et al. |
| 2014/0214149 A1 | 7/2014 | Kuraguntla et al. |
| 2014/0228878 A1 | 8/2014 | Scandurra et al. |
| 2015/0196303 A1 | 7/2015 | Seguin |
| 2015/0216531 A1 | 8/2015 | Seguin |
| 2015/0282859 A1 | 10/2015 | Bencini et al. |
| 2015/0352335 A1 | 12/2015 | Moeller |
| 2020/0046369 A1 | 2/2020 | Gainor et al. |

FOREIGN PATENT DOCUMENTS

| | | |
|---|---|---|
| DE | 19508129 | 9/1996 |
| DE | 102005060197 | 6/2007 |
| EP | 0366814 | 5/1990 |
| EP | 0959912 | 12/1999 |
| EP | 2016961 | 1/2009 |
| FR | 3016279 | 7/2015 |
| FR | 3017044 | 8/2015 |
| JP | 2005/538807 | 12/2005 |
| JP | 2007/526039 | 9/2007 |
| JP | 2009/502247 | 1/2009 |
| JP | 2009/509650 | 3/2009 |
| WO | WO 90/04430 | 5/1990 |
| WO | WO 90/06086 | 6/1990 |
| WO | WO 93/17731 | 9/1993 |
| WO | WO 95/10317 | 4/1995 |
| WO | WO-95/32018 A1 | 11/1995 |
| WO | WO 96/00095 | 1/1996 |
| WO | WO 96/12518 | 5/1996 |
| WO | WO 96/34647 | 11/1996 |
| WO | WO 98/50100 | 11/1998 |
| WO | WO 99/004833 | 2/1999 |
| WO | WO 00/66030 | 11/2000 |
| WO | WO 02/36048 | 5/2002 |
| WO | WO-2004/026112 A2 | 4/2003 |
| WO | WO 2004/026112 | 4/2004 |
| WO | WO 2005/084730 | 9/2005 |
| WO | WO 2006/020942 | 2/2006 |
| WO | WO 2006/067473 | 6/2006 |
| WO | WO 2007/014028 | 2/2007 |
| WO | WO 2007/038476 | 4/2007 |
| WO | WO-2007/038476 A2 | 4/2007 |
| WO | WO-2007/059594 A1 | 5/2007 |
| WO | WO-2008/154145 A1 | 12/2008 |
| WO | WO 2010/022173 | 2/2010 |
| WO | WO-2010/129089 A4 | 11/2010 |
| WO | WO 2012/017395 | 5/2012 |
| WO | WO-2013/109891 A | 7/2013 |
| WO | WO 2013/148697 | 10/2013 |
| WO | WO 2013/185138 | 12/2013 |
| WO | WO-2004/080338 A2 | 9/2014 |
| WO | WO 2015/107434 | 7/2015 |
| WO | WO 2015/114471 | 8/2015 |
| WO | WO-2015/133849 A1 | 9/2015 |
| WO | WO-2018/075552 A1 | 4/2018 |

OTHER PUBLICATIONS

PCT International Preliminary Report on Patentability in corresponding application PCT/US2011/061815, dated May 30, 2013, 16 pages.
International search report and written opinion dated Mar. 24, 2015 for PCT/IB/2015/050066.
International search report and written opinion dated Mar. 24, 2015 for PCT/IB/2015/050068.
Office action dated Sep. 28, 2015 for U.S. Appl. No. 14/594,012.
Office action dated Sep. 28, 2015 for U.S. Appl. No. 14/594,021.
Jan. 1, 2008, Borlaug, Ventricular-Vascular Interaction in Heart Failure, Heart Failure Clin 4 (2008) 23-36.
Jan. 1, 2011, Harnek et al., Transcatheter Implantation of the MONARC Coronary Sinus Device for Mitral Regurgitation, JACC: Cardiovascular Interventions, vol. 4, No. 1, 2011.
Jan. 1, 2007, Naeitje et al., Right ventricular function in pulmonary hypertension: physiological concepts, Eur Heart Journal Supplements (2007) 9 (supplement H), H5-H9.
Jul. 3, 2013, Procyrion, "A tool for the Cardiologist", Published Jul. 3, 2013, https:web.archive.org/web/20130703020540/http://www.procyrion.com/technology.
Jul. 1, 1971, Reuben, Compliance of the Human Pulmonary Arterial System in Disease, Circulation Research, vol. XXIX, Jul. 1971, pp. 40-50.
Jan. 1, 1983, Sunagawa et al., Left ventricular interaction with arterial load studied in isolated canine ventricle, Am J Physiol Heart CircPhysiol 245: H773-H780, 1983.
May 4, 2016, U.S. Office Action for U.S. Appl. No. 14/594,012 to Seguin, dated May 4, 2016.
May 24, 2008, Souza, Assessment of compliance in pulmonary arterial hypertension. European Heart Journal (2008) 29, 1603-1604 doi:10.1093/eurheartj/ehn181.
Mar. 17, 2008, Lankhaaret al., Pulmonary vascular resistence and compliance stay inversely related during treatment of pulmonary hypertension, European Heart Journal (2008) 29, 1688-1695 doi:10.1093/eurheartj/ehn103.
Dec. 31, 2010, Saouti et al., The arterial load in pulmonary hypertension, Eur Respir Rev 2010; 19: 117, 197-203.
Aug. 9, 2011, Wang et al., Pulmonary vascular wall stiffness: An important contributor to the increased right ventricular afterload with pulmonary hypertension. Downloaded from http://www.pulmonarycirculation.org on Aug. 9, 2011, IP: 173.200.213.20.
Dec. 31, 1973, Elizinga et al., Pressure and Flow Generated by the Left Ventricle against Different Impedences, Circ. Res. 1973;32:178-186.
Dec. 31, 1980, Elzinga et al., Left and right ventricular pump function and consequences of having two pumps in one heart. A study on the isolated cat heart, Circ. Res. 1980; 46:564-574.
Dec. 31, 1996, Grant et al., Clinical significance of pulmonary arterial input impedance, Eur Respir J, 1996, 9, 2196-2199.
Dec. 31, 2012, Lammers et al., Mechanics and Function of the Pulmonary Vasculature: Implications for Pulmonary Vascular Disease and Right Ventricular Function, American Physiological Society. Compr Physiol 2:295-319, 2012.
Feb. 6, 2006, Mahapatra et al., Relationship of Pulmonary Arterial Capacitance and Mortality in Idiopathic Pulmonary Arterial Hypertension, J. Am. Coll. Cardiol. 2006;47;799-803.
Jul. 11, 2014, Pellegrini et al., Prognostic Relevance of Pulmonary Arterial Compliance in Patients With Chronic Heart Failure, Chest 2014; 145(5):1064-1070.
Extended EP Search Report dated Feb. 6, 2018 in EP Patent Appl. Serial No. 11843546.0.
"Aria CV Wins Contest for Pulmonary Arterial Hypertension Medical Device," https://pulmonaryhypertensionnews.com/2018/09/27/aria-cv-wins-contest-pulmonary-arterial-hypertension-medical-device/, dated Sep. 27, 2018, (accessed Dec. 13, 2019).
"Aria CV wins top honors in device organization 'Shark Tank' competition," http://www.startribune.com/joe-carlson/271816721, dated Apr. 22, 2019, (accessed Dec. 13, 2019).
"Aria CV Awarded Top Prize At TCT's 2018 Shark Tank Competition", https://cathlabdigest.com/content/Aria-CV-Awarded-Top-Prize-TCT's-2018-Shark-Tank-Competition, dated Oct. 9, 2018, (accessed Dec. 13, 2019).
Brian, Jr., M.D., Johnny E., Associate Professor, Department of Anesthesia, University of Iowa College of Medicine, "Gas Exchange, Partial Pressure Gradients, and the Oxygen Window," Oct. 2001.
Extended EP Search Report dated Mar. 1, 2017 in EP Patent Application Serial No. 11792905.9.
Extended EP Search Report dated Jun. 19, 2019 in EP Patent Application Serial No. 19165162.9.
International Search Report & Written Opinion dated Dec. 22, 2015 in Int'l PCT Patent Application Serial No. PCT/US2015/036201.
International Search Report & Written Opinion for PCT/US2017/057035 dated Jan. 31, 2018.
International Search Report dated Sep. 8, 2011 in Int'l PCT Patent Appl. Serial No. PCT/US2011/38558.
International Search Report dated Jan. 31, 2018 in Int'l PCT Patent Appl. Serial No. PCT/US2017/057035.

(56) References Cited

OTHER PUBLICATIONS

Lategola, Michael T., Measurement of Total Pressure of Dissolved Gas in Mammalian Tissue In Vivo, J.Appl.Physiol., 19:322-4 (1964).
Loring, Stephen H., et al., Gas Exchange in Body Cavities, Handbook of Physiology—The Respiratory System IV, Chapter 15, pp. 283-295 (1987).
Piiper, Johannes, Physiological Equilibria of Gas Cavities in the Body, Handbook of Physiology. Section 3: Respiration, vol. II, pp. 1205-1218 (1965).
Second Written Opinion dated Jul. 7, 2016 in Int'l PCT Patent Application Serial No. PCT/US2015/036201.
Tenney, et al., Gas Transfers in a Sulfur Hexafluoride Pneumoperitoneum, Journal of Applied Physiology, 6(4):201-208 (1953).
Tucker, et al., Inert Gas Exchange in Subcutaneous Gas Pockets of Air-Breathing Animals: Theory and Measurement, Respiration Physiology, 1:151-171 (1966).

\* cited by examiner

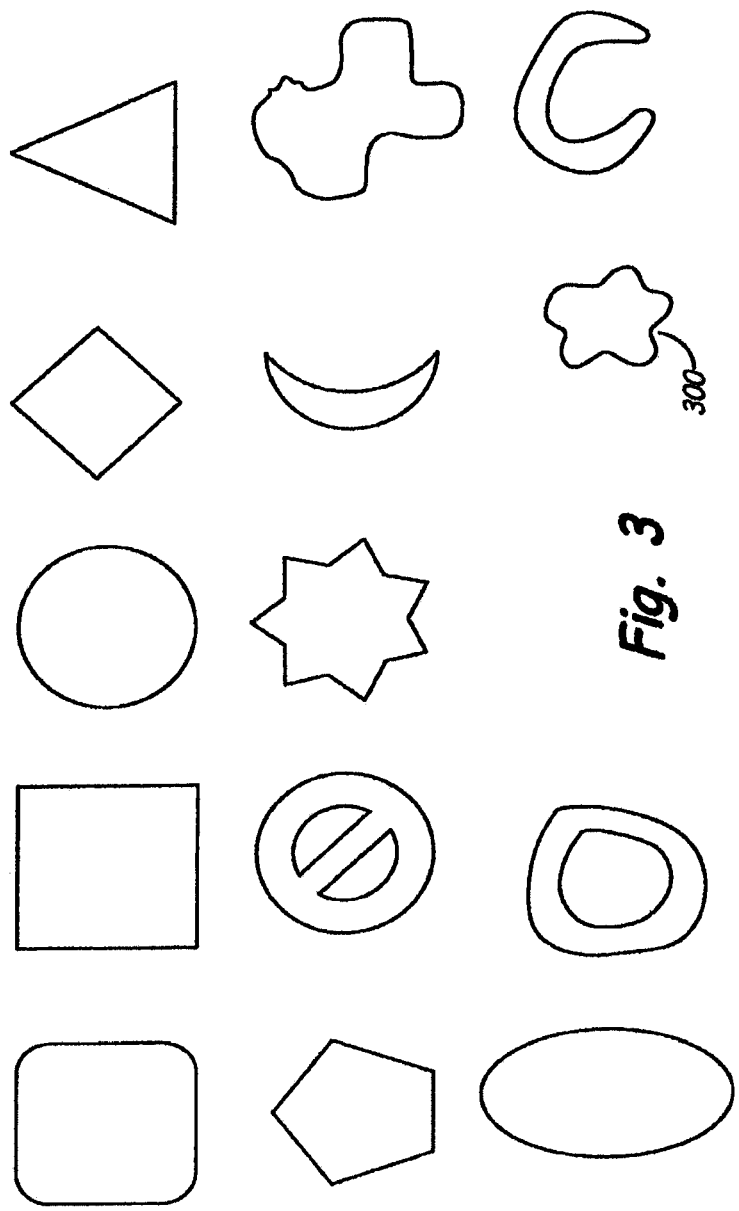

SYSTEM AND METHOD FOR REDUCING PULSATILE PRESSURE

This application is a continuation of U.S. application Ser. No. 14/253,127, filed Apr. 15, 2014, which is a continuation of U.S. application Ser. No. 13/884,169, issued Apr. 28, 2015 as U.S. Pat. No. 9,017,359, which was the National Stage of International Application No. PCT/US2011/061815, filed Nov. 22, 2011, which claims the benefit of U.S. Provisional Application No. 61/416,187, filed Nov. 22, 2010; and the entire contents of each of the forgoing applications are incorporated herein by reference.

FIELD OF THE INVENTION

The invention relates generally to a system and method for reducing pulsatile pressure, and more particularly to a device having a compliant body that is implantable in a vessel for reducing pulsatile load in the vessel and a method of delivering the device.

BACKGROUND OF THE INVENTION

In patients with pulmonary arterial hypertension, a known or unknown disease process results in vasoconstriction and proliferation of the cells making up the wall of the small pulmonary arteries. This leads to increased resistance to blood flow and increased steady state pressure in the pulmonary artery. Over time, the increased pressure in the pulmonary artery, as well as other disease processes, cause the pulmonary artery to lose its elasticity, resulting in a decrease in vascular compliance. Vascular compliance is a measure of the elastic properties of a vessel and is defined as the change in volume in a vessel in response to a change in pressure ($\Delta V/\Delta P$). A compliant vessel is able to accommodate a relatively large volume change for a given change in pressure. With each stroke of the heart, a volume of blood (stroke volume) is pumped from the right ventricle into the pulmonary artery. When the compliance is low, as occurs in pulmonary arterial hypertension, the right ventricle must produce a high pressure in order to pump each stroke volume into the pulmonary artery because the vessel is unable to stretch to accommodate the incoming blood. This results in a high pulse pressure, which is the arithmetic difference between the systolic and diastolic pressures.

The abnormally high stiffness of the arterial wall also affects the pulse wave velocity (PWV) so that reflected waves may contribute significantly to pulse pressure. PWV may be estimated by the Moens-Korteweg equation: $PWV = (E\ h/2R\rho)^{1/2}$. An important component of this equation is E or Young's modulus, a measure of stiffness of the arterial wall. In pulmonary arterial hypertension, Young's modulus may be greater than normal, resulting in a higher than normal PWV. With each heartbeat and ejection of blood, a temporary and localized increase in hydraulic pressure is created in the pulmonary artery. This pressure impulse propagates away from the heart as an acoustic wave. When the wave encounters an impedance discontinuity, such as an abrupt change in diameter or a branch, a reflection occurs. These reflections travel retrograde towards the heart. In a person with normal vascular stiffness and PWV, the major reflected wave reaches the heart after the ejection of blood. But with aging and the development of systemic hypertension, pulmonary arterial hypertension, arteriosclerosis, as well as other conditions, vascular stiffness and PWV may be increased, causing the major reflected wave to arrive at the heart earlier. In many patients with pulmonary arterial hypertension, the major wave can arrive during ejection, significantly contributing to the pulmonary artery pulse pressure and cardiac work.

In 1983, Sunagawa employed the concept of elastance as a change in pressure over change in volume (elastance is $\Delta P/\Delta V$, the reciprocal of compliance). (Sunagawa at al., Am J Physiol Heart CircPhysiol 245: H773-H780, 1983.) In normal, healthy individuals, the elastance of the pulmonary artery and the right ventricle are matched or coupled. Much like impedance matching in an electrical circuit, coupling represents a state of optimum stroke work and energetic efficiency. (Borlaug et al., Heart Fail Clin 4: 23-36, 2008.) The optimum value of the ratio of elastance of the right ventricle to the elastance of the pulmonary artery is between 1 and 2. (Naeitje et al., Eur Heart Journal Supplements (2007) 9 (supplement H), H5-H9.) In advanced stages of pulmonary arterial hypertension, this ratio is decreased, a condition termed afterload mismatch. (Borlaug, Ventricular-Vascular Interaction in Heart Failure, Heart Failure Clin 4 (2008) 23-36.) This decoupling indicates that additional energy is needed in order to maintain flow, thus imposing additional load on the right ventricle.

Thus, as appreciated by those of ordinary skill in the art, the relatively low compliance (or high stiffness) of the pulmonary artery in patients with pulmonary arterial hypertension leads to increased pulse pressure. It also leads to higher PWV, which causes reflected waves to contribute to afterload, further increasing pulse pressure. Furthermore, elastance decoupling leads to a state of energetic inefficiency and increased workload for the heart. These components combine to contribute to pulsatile load and increase the workload on the right ventricle.

In pulmonary arterial hypertension, the total load that the right ventricle must overcome to pump blood can be considered the sum of the steady state load (due to restriction of flow caused by small vessel constriction) and the pulsatile load (which is caused by decreased compliance or increased stiffness). While in the past most researchers and physicians focused on addressing the steady state load, many researchers now feel that pulsatile load may be of comparable importance in imposing a load on the heart.

In a normal, healthy individual, the pulmonary circulation operates at a substantially lower pressure than the systemic circulation. The pressure in the right ventricle is usually one-sixth of that in the left ventricle. In comparison to the left ventricle, the right ventricle is less capable of withstanding chronically elevated pressures and workloads. Initially, when exposed to high pressure the right ventricle adapts to the higher load via multiple mechanisms including hypertrophy, but as the pressure continues to rise, the heart loses this ability to compensate, eventually leading to right heart failure, a leading cause of death in pulmonary arterial hypertension.

Drugs are the mainstay of current therapy for pulmonary arterial hypertension. An important function of the pulmonary arterial hypertension-specific drugs is to dilate the small pulmonary arteries. These medications tend to lower the steady state load by increasing the cross-sectional area of the constricted vessels, but do not directly target the elevated pulsatile load caused by lack of compliance.

To summarize, many pulmonary arterial hypertension patients die of right heart failure due to chronically elevated load on the right ventricle. Increased pulsatile load is a significant component of the total load and is caused by a relative lack of compliance in the pulmonary artery. Current therapy is not directed at improving compliance. Thus, there is a need for a solution to lower pulsatile load by increasing compliance of the pulmonary artery.

BRIEF SUMMARY OF THE INVENTION

The invention addresses the foregoing problems by providing a device for reducing pulsatile load in an artery that includes a reservoir, an injection port, a transvascular conduit, and a compliant body. The internal cavities of the components are fluidly coupled to one another, allowing gas to move and pressure to equalize between the components. The reservoir may be located under the skin in the area of the subclavian vein or in another suitable location remote to the compliant body. The injection port, which allows for filling and pressure adjustments of the reservoir, may either be attached to the reservoir by an extravascular conduit or mounted directly to the reservoir body. The transvascular conduit passes through the subclavian vein, superior vena cava, right atrium, and right ventricle and connects the reservoir to the compliant body. The compliant body may be located in the pulmonary artery and consists of a flexible membrane surrounding a compressible or noncompressible gas or other suitable fluid.

Implantation of the device may be performed by means of a minimally invasive procedure using local anesthesia and fluoroscopy. For example, a first incision may be made in the subclavicular skin and a second incision or window may be made in the subclavian vein. A pocket may be formed in the subcutaneous space adjacent to the first incision that is sized for placement of the reservoir. The distal end of the compliant body may be inserted into the subclavian vein incision with the device deflated. The compliant body and conduit may then be advanced until the compliant body reaches the desired resting position in the pulmonary artery. Although not necessary, a sheath and/or a wire may be used to guide the device into place within the vasculature. Once the compliant body is properly situated within the pulmonary artery, the reservoir may be placed in the subcutaneous pocket and the incision closed. As will be appreciated by those of ordinary skill in the art, the compressible gas may be injected into the reservoir through the injection port either before or after the incision is closed.

BRIEF DESCRIPTION OF THE DRAWINGS

FIG. 3 is a diagram illustrating exemplary cross-sectional geometries of a compliant body in accordance with the invention.

DETAILED DESCRIPTION OF THE INVENTION

Generally speaking, the invention is directed to the treatment of pulmonary arterial hypertension by improving compliance of the pulmonary vasculature. In one exemplary embodiment, a gas-filled compliant body is positioned in the pulmonary artery. Mimicking how a normal pulmonary arterial vasculature stretches to accommodate each stroke volume, the gas in the compliant body compresses to accommodate this volume. By adding a compliant body to the pulmonary artery, the system is able to accept blood volume without causing a large change in pressure, i.e. the compliance or $\Delta V/\Delta P$ is increased. One embodiment comprises a compliant body attached to a reservoir by means of a hollow conduit. The reservoir is, in turn, connected to a filling or injection port by means of an extravascular conduit. In this configuration, the various components are fluidly coupled with one another such that gas can flow and/or pressure can equalize between all the components.

The device of the invention is operable to decrease peak pressure in the pulmonary artery with minimal change in mean pressure. The putative mechanisms of peak pressure reduction are achieved directly through increased compliance and indirectly by slowing the PWV thereby reducing the contributions from reflected waves. As appreciated by those of ordinary skill in the art, lowering peak pressure decreases the pathologic toll on the right ventricle by reducing peak right ventricular wall stress and mechanical work. In addition, by increasing compliance (i.e. decreasing elastance), the device improves the elastance coupling of the pulmonary artery and right ventricle, thus representing a state of increased energetic efficiency. In addition, reducing peak pressure may help slow the progression of the disease in the small arteries by reducing strain on the calcium channels and lowering the stimulus for pathologic remodeling. In total, these benefits result in decreased workload on the heart and improved quality and duration of life for patients suffering from pulmonary arterial hypertension.

Figure 1:
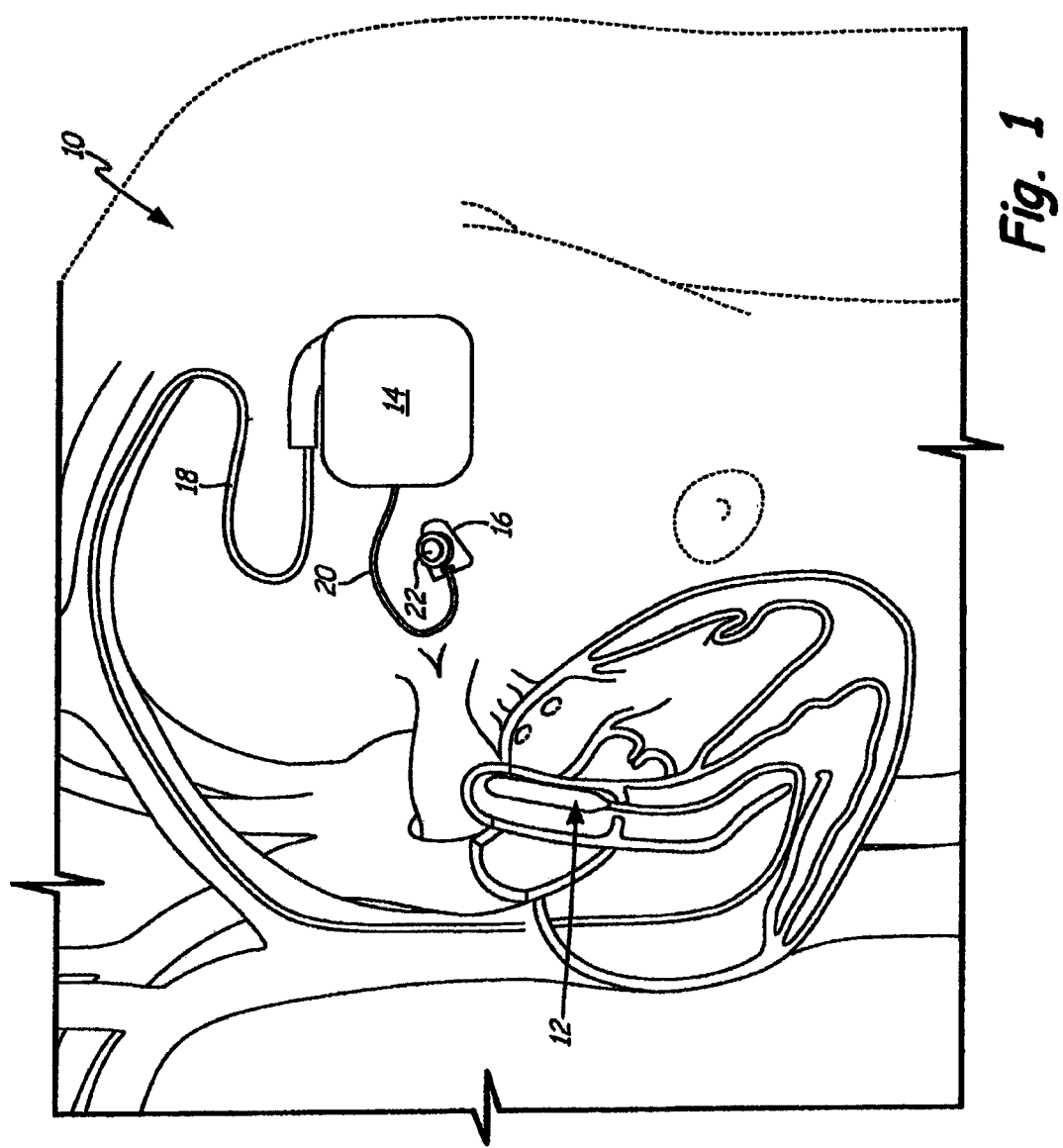
FIG. 1 is a diagram illustrating a first exemplary embodiment of a pressure reducing device in accordance with the invention.

FIG. 1 is a diagram illustrating a first exemplary embodiment of a pressure reducing device 10 in accordance with the invention. As illustrated in FIG. 1, the device 10 generally includes a compliant body 12, a reservoir 14, an injection port 16, a transvascular conduit 18 extending between the compliant body 12 and the reservoir 14, and an extravascular conduit 20 extending between the reservoir 14 and the injection port 16. The internal cavities of the foregoing components are "continuous," thereby allowing gas to move and pressure to equalize between the components.

More particularly, in the exemplary implantation position illustrated in FIG. 1, the reservoir 14 is located in the subcutaneous space near the subclavian vein while the compliant body 12 is located in the pulmonary artery. The injection port 16 is attached to the reservoir 14 by means of the extravascular conduit 20 and allows for gas filling and pressure adjustments of the reservoir 14 and compliant body 12. The transvascular conduit 18 connects an internal cavity of the reservoir 14 to an internal cavity of the compliant body 12, and may pass though the heart much like the leads of a pacemaker.

Although the device 10 may be implanted within a patient in any suitable manner, one exemplary method of implantation is performed by a minimally invasive procedure using local anesthesia and fluoroscopy. In this type of procedure, an incision may first be made in the subclavicular skin and a pocket formed in the subcutaneous space. Then, an incision may be made in the subclavian vein. Upon forming the first and second incisions, a distal end of the compliant body 12 may be inserted into the subclavian vein incision with the body deflated or inflated. The compliant body 12 and transvascular conduit 18 may then be advanced until the compliant body 12 reaches the desired resting position in the pulmonary artery. As will be appreciated by those of ordinary skill in the art, a sheath or a wire may be used to guide the compliant body 12 and transvascular conduit 18 into place. With the compliant body 12 positioned in the desired resting position, the reservoir 14 may then be placed in the subcutaneous pocket and the incisions closed. Gas may then be injected into the injection port 16 to fill the device. Alternatively, the device may be filled with gas prior to closing the incision in the subclavicular skin. Alternatively, part of the device 10 may be filled with a liquid which has a vapor pressure of approximately 1 atmosphere at body temperature. As the gas diffuses through the walls of the device 10 the decrease in vapor pressure allows more to evaporate.

Figure 10A:
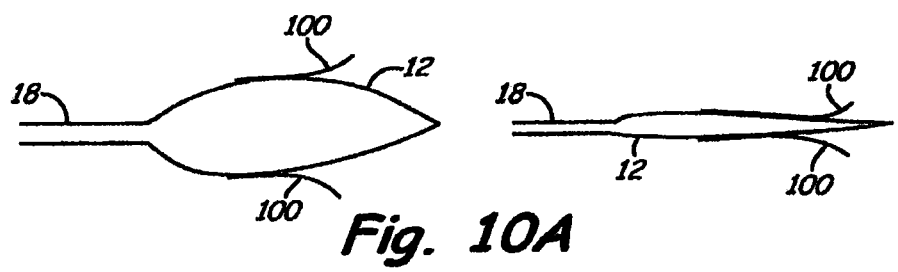
FIGS. 10A to 10E are diagrams illustrating exemplary anchoring devices and methods.
Figure 10B:
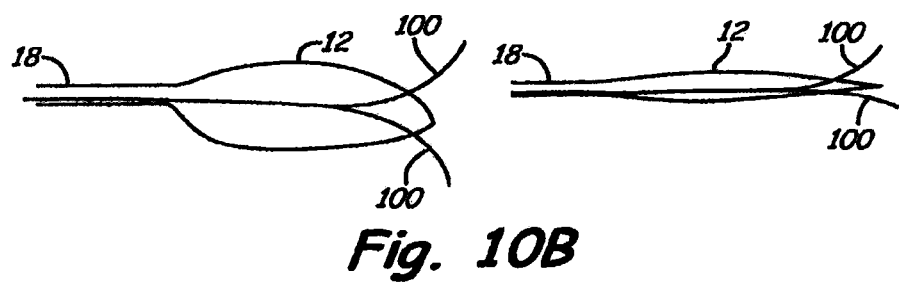

To limit the movement of the compliant body 12 when placed in the pulmonary artery, it may be beneficial to include an anchoring mechanism. As will be appreciated by those of ordinary skill in the art, this may be accomplished in a variety of ways, as illustrated in FIGS. 10A to 10E. Spring loaded anchoring members 100 may lay near the longitudinal axis when the compliant body is deflated then protrude radially to make contact with the innermost layer of the pulmonary artery when the complaint body is inflated. The anchoring members may protrude through the membrane when inflated then retract when deflated, as shown in FIG. 10B. The anchoring members may be mounted on the surface of the membrane FIG. 10A. When-released during inflation of the compliant body, they spring out to contact the walls of the artery. Subsequent deflation of the compliant body will retract them.

Figure 10C:
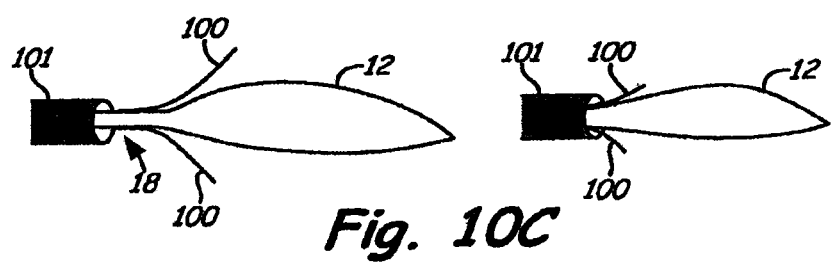

Alternately the members 100 may be compressed by a sheath 101 that encases the compliant body 12 and transvascular conduit 18 during the implant procedure, as shown in FIG. 10C. Removal of the sheath allows the members to spring out and contact the walls of the arteries. Re-introduction of the sheath retracts the members.

Figure 11A:
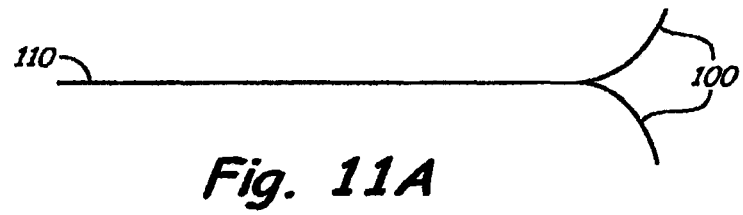
FIGS. 11A to 11C are diagrams illustrating exemplary anchoring devices and methods.
Figure 11B:
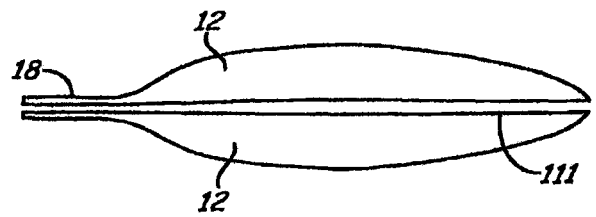
Figure 11C:
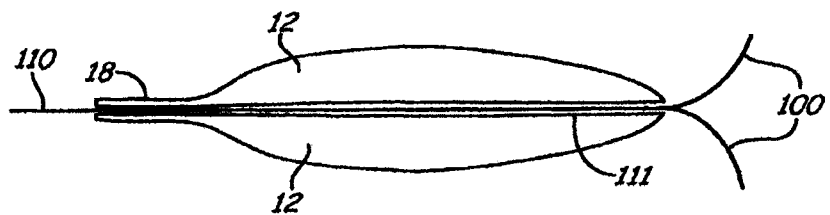

Alternately the anchoring mechanism may be separate from the compliant body and may consist of anchoring members 100 on the end of a guide wire 110 that pass out of the vasculature with the transvascular conduit 18 as shown in FIG. 11A to 11C. The compliant body 12 and conduit 18 may be designed with a lumen 111 that is continuous and isolated from the device lumen. Such a lumen would allow the device to be passed over the guide wire 110 until the body 12 and conduit 18 are in the desired location. The compliant body 12 and conduit 18 can then be removed and replaced or exchanged as needed while the anchoring system remains in place.

Figure 12A:
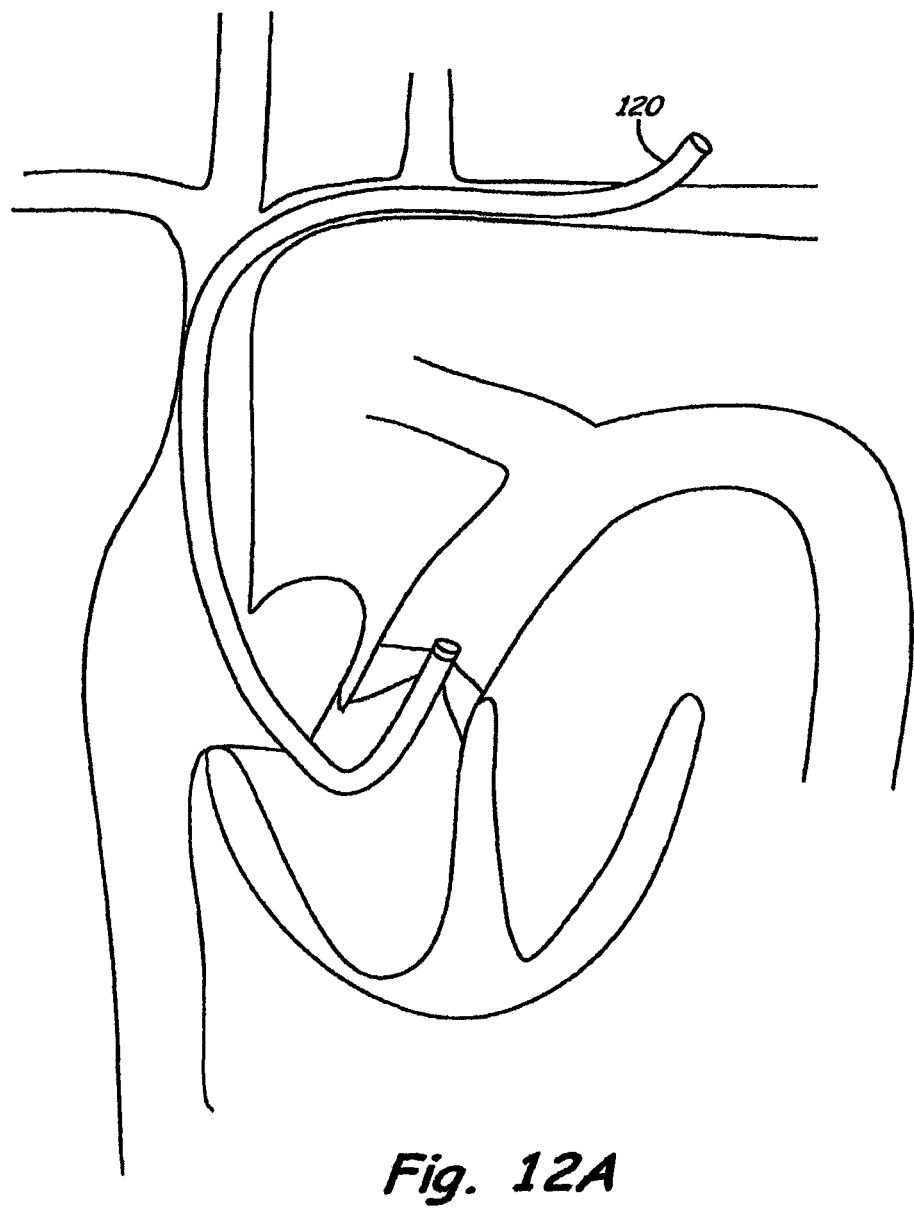
FIGS. 12A and 12B are diagrams illustrating an exemplary device for use in the method in accordance with the invention.
Figure 12B:
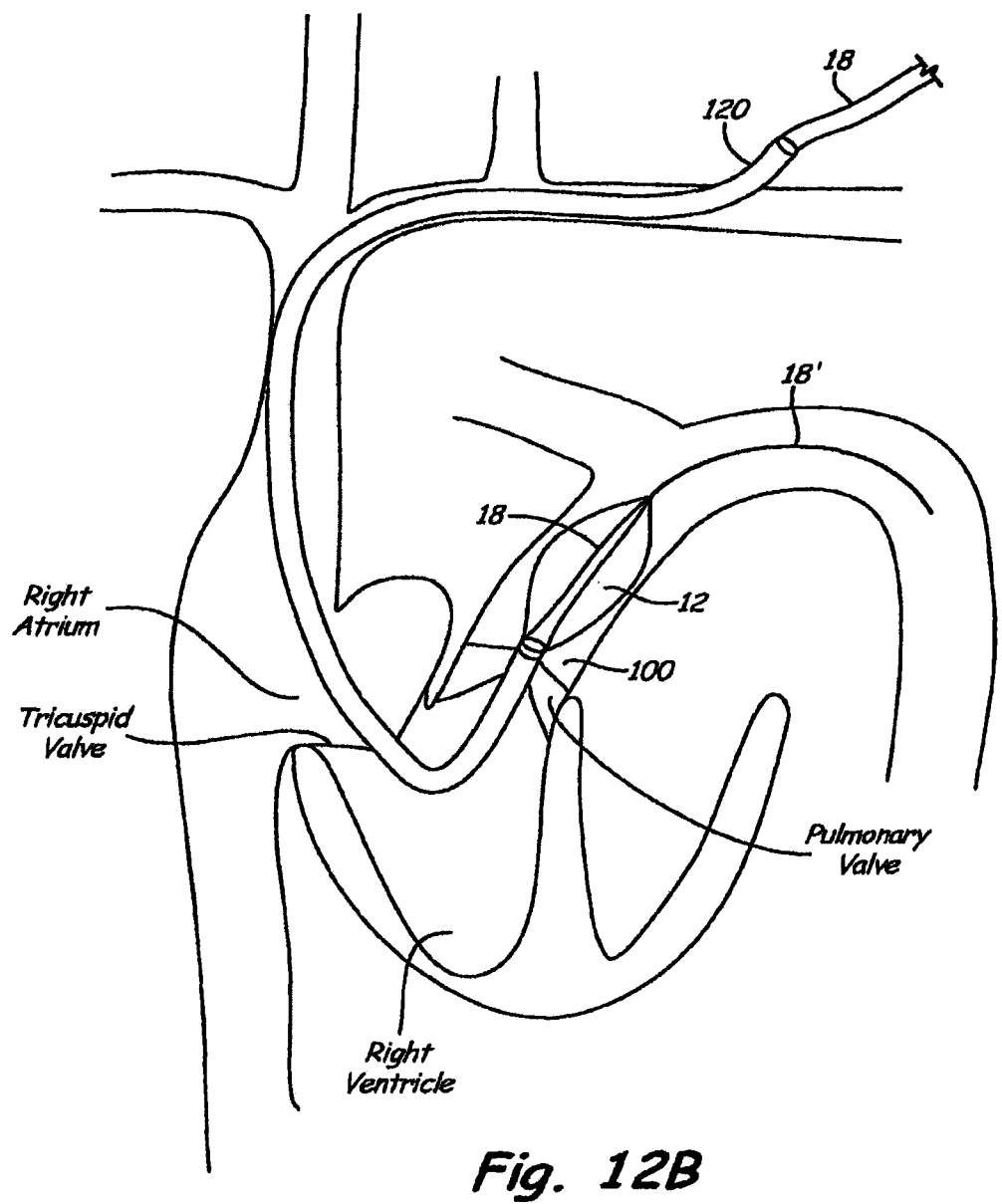

Referring now to FIGS. 12A and 12B, alternatively a permanently implanted introducer or sheath 120 may be used to create a passage from the subcutaneous space outside the blood vessel, through the vessel wall and to the desired site of device placement. The introducer 120 is positioned during the initial procedure. Anchoring mechanisms may or may not be attached to the introducer 120 to anchor it in a vessel in a patient and to anchor it in the pulmonary artery of a patient. Those of skill in the art will appreciate that the introducer 120 may be shaped to a beneficial shape minimizing or removing the need for anchoring mechanisms. The compliant body 12 operably coupled to the transvascular conduit 28 may be passed through the introducer 120 and introduced into the pulmonary artery with or without other guidance. This would allow for easy replacement of the compliant body 12 as needed. If it is found that the compliant body and transvascular conduit need to be removed, repositioned or exchanged they can be retracted or moved through the lumen (not shown) of the implanted introducer 120. Among other things the implanted introducer prevents the transvascular conduit from being encapsulated by the vascular wall as pace maker leads often are, offers support to the transvascular conduit and provides an anchoring platform that may not need to be removed.

Figure 10D:
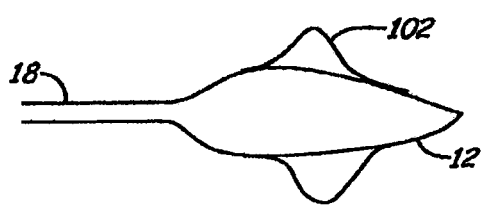

Referring to FIGS. 10D and 10B, the compliant body may alternatively be designed with integrated anchoring members 100 inherent in the shape of the compliant body. Anchoring members in the form of wings, fingers, fins, or like protuberances, may protrude from the surface or side of the compliant body 12 to center or wedge compliant body 12 in the vessel 103. Exemplary embodiments of such anchoring members are depicted in FIGS. 10D and 10E at 102, 104, respectively.

Figure 10E:
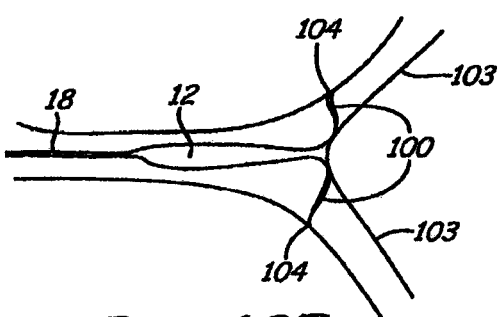

Anchor members 100 may pass through the main pulmonary artery bifurcation FIG. 10E, contacting the distal vessel wall 103 before bending back to touch the proximal vessel wall 104 downstream of the bifurcation.

Alternatively, conduit 18 may be used to anchor the compliant body 12. Conduit 18 may be anchored in the right ventricle or proximate the pulmonary valve or valve annulus or the wall of the pulmonary artery. It may be anchored with transmural anchors, hooks, lead screw type anchors or finger type entanglement anchors. The anchors may be removable and allow the conduit 18 and compliant body 12 to be easily removed.

Reservoir 14 may be free floating within a pocket in the tissue or may be fastened in place with sutures and appropriate suture fixtures.

As will be appreciated by those of ordinary skill in the art, one or more of the components of the device 10 may be implanted in another location without departing from the intended scope of the invention. Thus, the compliant body 12 and the reservoir 14 are described as being implanted in the pulmonary artery and the subcutaneous space beneath the subclavicular skin, respectively, for purposes of example and not limitation. Furthermore, the compliant body 12 may be implanted in the pulmonary artery via a pathway other than the subclavian vein without departing from the intended scope of the invention. Additionally, the device 10 of the invention may have use outside of reducing pulsatile load in an artery as will be appreciated by those of ordinary skill in the art.

Pressure in the pulmonary artery varies with each heartbeat. When the heart contracts (systole) and ejects blood into the pulmonary artery, the pressure in the artery is relatively high. When the heart is filling (diastole) and in between beats, the pressure is relatively low. In a normal, healthy individual, the pulmonary artery is very compliant. Its elastic nature allows it to stretch to accommodate the incoming blood without a large increase in pressure. In patients with pulmonary arterial hypertension, for example, the artery walls are abnormally stiff. As a result, the heart must produce a higher pressure in order to pump the same amount of blood into the pulmonary artery. Much like a normal pulmonary artery expands to make room for the incoming blood, the compliant body 12 of the device 10 compresses to make room for the blood being pumped through the pulmonary artery. This increases the compliance of the pulmonary artery and results in reduced systolic pressure in the pulmonary artery and right ventricle. The lower pressure reduces the workload of the heart, ultimately preventing or delaying the formation of right heart failure, a leading cause of death in patients with pulmonary arterial hypertension.

Figure 2A:
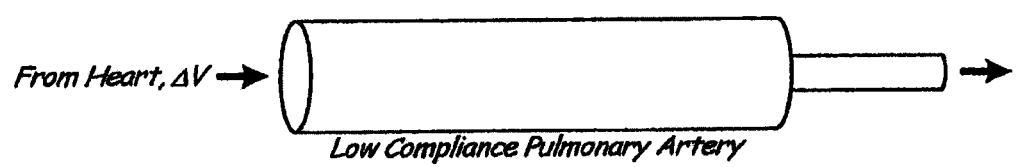
FIGS. 2A and 2B are diagrams illustrating the mechanical basis for the operation of the invention.
Figure 2B:
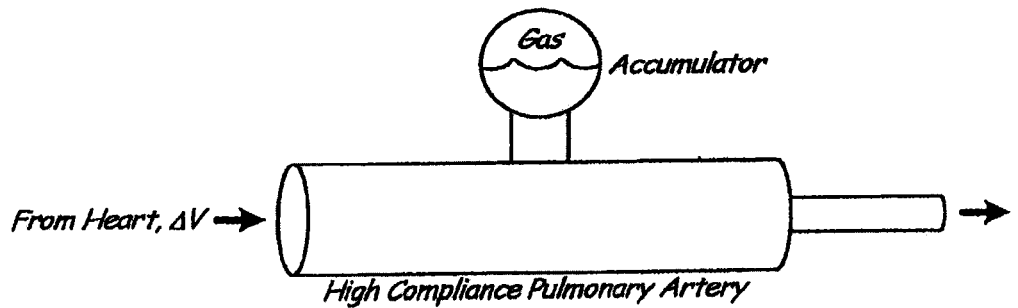

The mechanical basis of the pressure reducing device of the invention may generally be represented by an accumulator. As appreciated by those of ordinary skill in the art, accumulators are pressure storage reservoirs that may be employed in plumbing systems to minimize pressure fluctuations in a pipe. FIGS. 2A and 2B are diagrams illustrating the mechanical basis for the operation of the invention. Particularly, FIG. 2A is a diagram illustrating a pulmonary artery having a low vascular compliance, while FIG. 2B is a diagram of the same pulmonary artery with a means (i.e. the accumulator) for increasing the vascular compliance. With regard to FIG. 2A, during contraction of the heart the mitral valve is closed. Therefore, the predominant way blood ejected from the right ventricle may be accommodated is by expansion of the pulmonary artery. However, when the artery is "stiff" and has low compliance, there is a large increase in arterial pressure due to the inelasticity of the artery. Turning next to FIG. 2B, adding an accumulator to the low compliance artery of FIG. 2A results in an artery that once again has a high compliance. Specifically, although the artery itself is still stiff, the gas-filled accumulator allows the volume in the artery to change during systole with minimal change in pressure. Thus, the overall compliance of the artery is increased even though the elasticity of the artery does not change.

Relating the foregoing discussion to the operation of the device 10, during systole the gas contained within the compliant body 12 compresses. During diastole and between beats (when pressure in the pulmonary artery is relatively low) the gas in the compliant body 12 expands. Consequently, the device 10 reduces the peak (systolic) pressure in the pulmonary artery and boosts the pressure in the pulmonary artery during diastole. By lowering the pressure when the heart is ejecting blood, and raising the pressure in the pulmonary artery when the heart is not ejecting blood, the device reduces the mechanical load on the right ventricle without adversely affecting blood flow rate.

Now that the general structure and operation of the pressure reducing device 10 have been described, numerous design features of the various components will be set forth in detail. However, it should be understood that the particular components and their corresponding design features are described merely for purposes of example and not limitation. Thus, numerous other components and/or design features are contemplated and within the intended scope of the invention.

The compliant body 12 is a hollow, expandable vessel defined by an outer membrane that is structured for containing a compressible gas therein. The compliant body may be formed from elastic material (like a child's rubber balloon) or from a flexible but inelastic material (like the metalized mylar used in helium balloons). The balloon may be inflated so the surface is taut or may be inflated slightly less so the surface is not taut. The compliant body may also be multiple layers of multiple materials with one or more layers being formed of composite materials with reinforcing fibers. The compliant body 12 is preferably sized such that it may be positioned within the lumen of the pulmonary artery or other components of the cardiovascular system such as the aorta, right or left atrium, or right or left ventricles. The entire compliant body 12 may be located within the cardiovascular system or some or all of it may be located outside the cardiovascular system. Furthermore, even when positioned completely within the cardiovascular system, the entire compliant body 12 may be located in the lumen of a cardiovascular body part or it may extend into multiple lumina, such as in the lumen of the right ventricle and the lumen of the pulmonary artery or branches of the pulmonary artery.

Figure 9A:
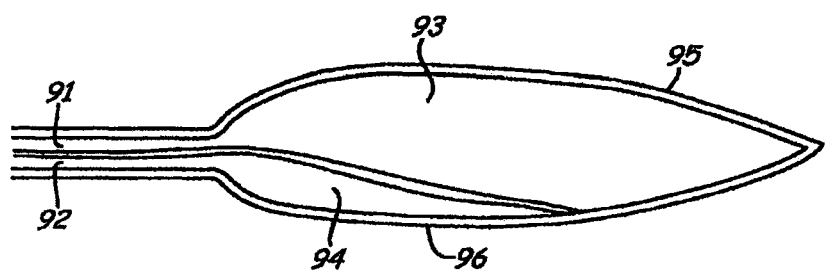
FIGS. 9A and 9B are diagrams illustrating exemplary cross-sectional geometries of a compliant body with multiple chambers.
Figure 9B:
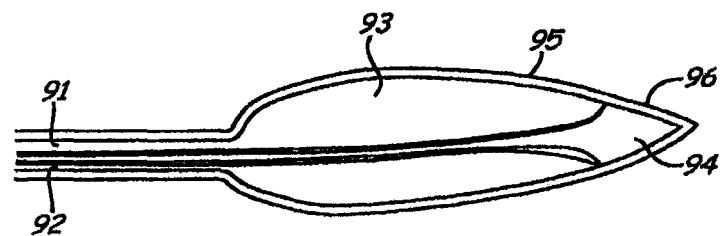

The internal cavity of the compliant body 12 that is structured for holding the compressible gas is fluidly coupled to the lumen of the transvascular conduit 18. In some embodiments, the compliant body 12 may include more than one internal cavity. For example and referring to FIGS. 9A and 9B, in some embodiments a plurality of internal cavities 93, 94 may exist in the compliant body 12 each with their own lumens 91, 92, respectively, each fluidly coupled to the transvascular conduit 18, extravascular conduit 20, reservoir 14, port 16 and septum 22, as the case may be. One or multiple cavities may be operated at different pressures or volumes. One or multiple cavities may be dedicated to the delivery of therapeutics through diffusion through the associated cavity membranes 95, 96 or from direct orifices from the lumen to the blood.

As illustrated in FIG. 1, the shape of the compliant body 12 may be an elongated cylinder with tapered or rounded ends to reduce drag. The long, thin design of the compliant body 12 minimizes the cross-sectional area and resistance to flow caused by the device, and at the same time lowers PWV.

Although the compliant body 12 of FIG. 1 includes a generally cylindrical cross-sectional shape, numerous other cross-sectional shapes are also possible and within the intended scope of the invention as illustrated in FIG. 3. These cross-sectional shapes may be, for example, crescent shaped, cylindrical with cut-outs, fluted, oval, or the like. As will be appreciated by those of ordinary skill in the art, the cross-sectional shapes illustrated in FIG. 3 are provided merely for purposes of example and not limitation. The compliant body 12 may be of varying cross sectional shape along its length. The compliant body may have a central lumen to accommodate a guide wire. The compliant body 12 may be designed to equally distribute stress across the body and prevent local stress concentrations. This may be achieved by forming the surface of the compliant body 12 from a series of radiuses 300 such as to prevent stress concentration in sharp corners. This principle may be applied to any of the shapes in FIG. 3.

Figure 15A:
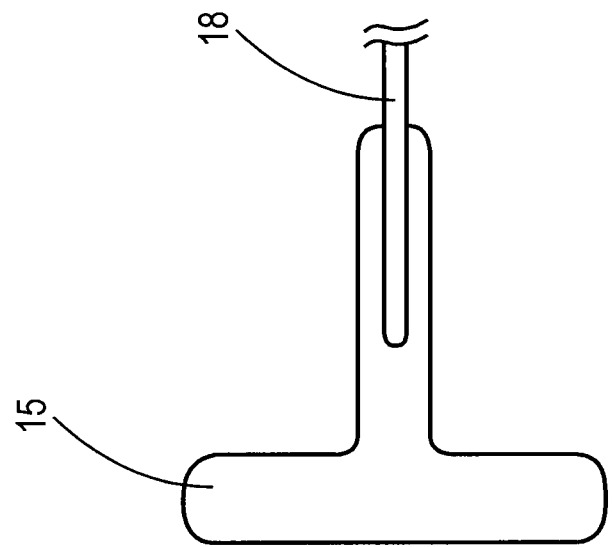
FIGS. 15A and 15B are diagrams illustrating exemplary cross-sectional geometries of compliant bodies in accordance with the invention.
Figure 15B:
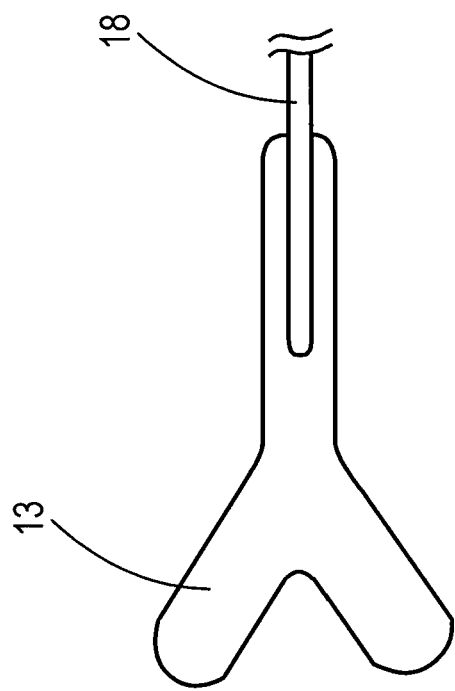

Referring to FIGS. 15A and 15B, the distal end of the compliant body (opposite the transvascular conduit attachment site) may be Y or T shaped, such that arms of the compliant body may be inserted into branches of vessels. For example, as shown in FIG. 15A, the distal end of the compliant body 13 may be Y shaped, or as shown in FIG. 15B, the distal end of the compliant body 15 may be T shaped. Embodiments having more than two arms are also contemplated.

Figure 13:
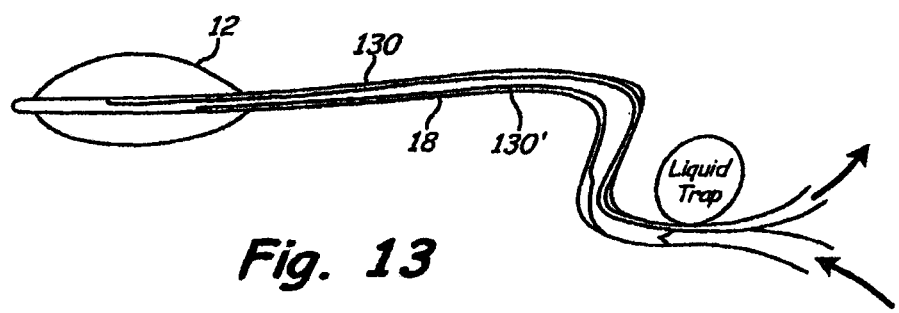
FIG. 13 is a diagram illustrating multiple fluidly independent lumens in the transvascular conduit in accordance with the invention.

The compliant body 12 may contain one or more sensors for monitoring one or more physical properties of the cardiovascular system where it is located, or alternatively for monitoring various parameters of the pressure reducing device 10. Examples of such properties and parameters include, but are not limited to, temperature, pressure, flow rate, oxygenation, $CO_2$ concentration, pH, luminal diameter, and the like. Markers may also be attached to or incorporated into the perimeter of the compliant body 12 for imaging as will be discussed in further detail below. As will be appreciated by those of ordinary skill in the art, the device 10 may have multiple independent lumens in the conduits 18, 20 with multiple corresponding ports 16 and septums 22 in fluid connection to multiple orifices located on or near the compliant body and transvascular conduit 18 for the purpose of measuring common hemodynamic parameters. Referring to FIG. 13, the device may include a plurality of fluidly independent lumens 130, 130' from the injection port to the compliant body 12. These lumens may be of varying sizes and with varying independent internal coatings and varying passages from the lumen to the interior of the compliant body. It may be beneficial to have a lumen with a hydrophilic coating with a second lumen with a hydrophobic coating such that any absorbed and condensed water vapor enters the hydrophilic lumen and condenses. Dry gas can be introduced into one of the lumens while water and moist gas can be drawn out the other. In this way the system can be purged and dried. The device may be configured with multiple lumens and one-way valves on one or multiple lumens such that gas flows to the compliant body through one lumen and returns from the compliant body through another lumen. The return lumen may pass through a liquid trapping device to trap condensed liquid acting as a desiccator-like trapping mechanism.

Figure 14A:
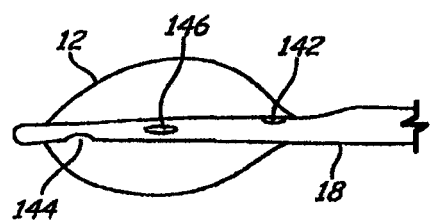
FIGS. 14A and 14B are diagrams illustrating exemplary devices in accordance with the invention.

Referring to FIG. 14A, the device may have one or more openings 142, 144, 146 from the lumen to the interior of the compliant body and they may be arranged in a particular order radially around the lumen and along the length of the compliant body to prevent them from being blocked when the compliant body collapses.

Figure 14B:
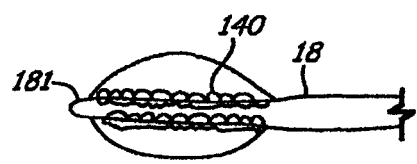

Referring to FIG. 14B, the transvascular conduit 18 may pass through the compliant body 12 and extend past 18' the compliant body 12. The surface of the conduit 18 within the compliant body 12 may be coated with compliant material or porous compliant material 140 which acts to cushion the surface of the conduit. Suitable materials may include polymers, open cell foamed rubber, foamed rubber, silicones, woven or knitted fibers, dense brush-type materials such as Velcro and the like. Such coatings 140 will prevent acoustic pressure spikes in the surrounding blood when the compliant body collapses completely.

Referring again to FIG. 12B the distal tip 18' of the transvascular conduit may extend past the compliant body. Anchoring mechanisms may be mounted on this extended tip 18', or the extended tip may follow the curvature of the vasculature and assist in centering and curving the compliant body so it follows the shape of the vessel.

The compliant body 12 is sized such that when it is inflated to the predetermined pressure or volume, the cross sectional area that is taken up in the pulmonary artery is minimized as shown in FIG. 1. Inasmuch the compliant body 12 is formed of a flexible material and its internal gas is compressible, during systole the systolic blood pressure will cause the compliant body 12 to contract to a contracted state, whereupon the volume which it takes up within the pulmonary artery will be reduced. This contracting action has the effect of absorbing or reducing the systolic pressure and also reducing the rate of change (i.e. acceleration) of blood flow.

During diastole the reduced diastolic pressure enables the gas within the compliant body 12 to expand to cause the compliant body 12 to assume its expanded state again, thereby releasing the absorbed portion of the systolic blood pressure. Thus, the repeated contracting and expanding action of the compliant body 12 reduces the difference between peak systolic pressure and diastolic pressure, all the while maintaining average blood pressure and blood flow. Consequently, cardiac workload is reduced without a concomitant reduction in cardiac output.

The volumetric capacity of the compliant body 12 is selected such that it can collapse to absorb enough of the ventricular ejection volume to significantly lessen peak systolic pressure. Since the heart of an adult typically ejects 2-6 liters per minute, the ejection or stroke volume per contraction of the heart will generally be between 25-100 ml (assuming a pulse rate range of 60-80 beats per minute), with most patients having a stroke volume of about 60 ml. In order to meaningfully reduce the systolic pressure of such persons, it is contemplated that the compliant body 12 should have a volumetric capacity so that when it is in the expanded state during diastole it displaces at least about 5 ml of blood volume within the pulmonary artery (for pediatric applications the volumetric capacity may be less, such as about 1 or 2 ml). In order to achieve this result, in one exemplary embodiment the pressure reducing device 10 is injected with between about 60 and about 1000 ml of gas (distributed between the compliant body 12 and the reservoir 14). Accordingly, when the compliant body 12 is compressed by systolic pressure it can affect a significant reduction in systolic pressure. Compliant bodies with larger capacities may be used to provide even greater reductions in the systolic pressure so long as they are suitable for disposition within the vascular system.

As will be appreciated by those of ordinary skill in the art, any suitable biocompatible gas may be used in the pressure reducing device 10. In one exemplary embodiment, the gas is a compressible gas such that its volume changes in response to a change in pressure in the artery (or other implantation location of the compliant body 12) consistent with the gas bulk modulus of the gas. Furthermore, the gas is preferably nontoxic, easily absorbed by the body, and has physical properties that resist diffusion through the compliant body membrane. Suitable gases may include, but are not limited to, nitrogen and carbon dioxide. Optionally, the gas may have therapeutic properties, such as nitric oxide which causes vasodilation.

The membrane of the compliant body 12 that encapsulates the volume of gas may be formed from a thin, sheet-like structure comprising one or more materials or layers. As will be appreciated by those of ordinary skill in the art, any suitable material that is both biocompatible and flexible may be used that enables pressure changes external to the compliant body to be transmitted to the gas. The use of a biocompatible material is important to enable the compliant body 12 to perform its function in the body without eliciting an undesirable local or systemic response. In order to preserve the injected volume of gas within the pressure reducing device 10, a membrane material that minimizes diffusion of gas through the membrane may be preferable. Additionally, the membrane may be elastic, such that the compliant body 12 can return to its original shape after deformation, and resistant to fatigue, such that the compliant body 12 maintains its strength and integrity after multiple deformations.

In order to prevent thrombus formation after implantation, the membrane is preferably antithrombotic. As will be appreciated by those skilled in the art, the membrane surface may be biomimetic or have inherent antithrombotic properties or its external surface may be coated with a material to prevent thrombus formation, such as heparin or the like. Additionally, the membrane may be lubricious, such that it impedes adhesion of body components such as platelets, proteins, endothelium, endocardium, or heart valves. Any suitable biocompatible lubricant may be used including, but not limited to, silicone or hyaluronan based materials. The shape of the membrane may also be carefully defined to eliminate dead space in the surrounding blood flow to minimize thrombus formation.

In some embodiments, it may be preferable to select a membrane material that is MRI compatible. Radio-opaque or other markers may be incorporated or attached to the compliant body 12 for imaging. The use of such marker elements allows for viewing of the compliant body with a suitable imaging system, such as x-ray, MRI scanner or fluoroscopic system. As will be appreciated by those skilled in the art, any suitable marker elements and imaging system may be used without departing from the intended scope of the invention.

Turning next to the reservoir 14, this component resembles a hollow, thin-walled vessel that is structured for receiving the compressible gas therein. The reservoir 14 is preferably sized such that it may be positioned within the subcutaneous space in the region of the right or left subclavian veins. However, the reservoir 14 may be positioned within any suitable body cavity having sufficient space without departing from the intended scope of the invention. Although any suitable shape may be used, in one exemplary embodiment the reservoir 14 may be a rounded, flattened disk to minimize protrusion through the patient's skin.

The interior cavity of the reservoir 14 is in fluid communication with the interior cavity of the compliant body 12 via a lumen of the transvascular conduit 18 such that gas may move between the cavities and/or pressure may equalize between the cavities. The interior cavity of the reservoir 14 is also in fluid communication with the injection port 16 via a lumen of the extravascular conduit 20 such that gas may move between the reservoir 14 and the injection port 16 and/or pressure may equalize between them.

As will be appreciated by those of ordinary skill in the art, the reservoir 14 may be formed from any suitable material or materials that prevent or minimize diffusion of the gas from the internal cavity through the outer walls. However, the material must be biocompatible such that it is able to perform its function in the body without eliciting an undesirable local or systemic response. Similar to the compliant body 12, the reservoir material may also be MRI compatible. Radio-opaque or other markers may be incorporated into the perimeter of the reservoir 14 for imaging. The use of such marker elements allows for viewing of the reservoir with a suitable imaging system.

Optionally, the external surface of the reservoir 14 may be lubricious, such that it impedes adhesion of body components such as platelets or proteins. Exemplary but not limiting lubricants may include silicone or hyaluronan based materials.

The reservoir 14 may contain one or more sensors for monitoring one or more parameters of the pressure reducing device 10. Examples of such parameters include, but are not limited to, the gas pressure or volume within the reservoir 14. As appreciated by those of ordinary skill in the art, such measurements may be used to determine when filling of the reservoir is required.

In some embodiments, the reservoir 14 may contain electrical leads and couplings for transmitting signals to and from the compliant body 12 and/or the injection port 16. The reservoir 14 may also contain a transmitter and receiver for sending and receiving telemetric signals to/from an external station. For example, the signals may be used to transmit the properties or parameters monitored by the reservoir 14 and/or compliant body 12, such as volume, pressure, temperature, flow rate, oxygenation, $CO_2$ concentration, pH, luminal diameter, or the like. Additionally, the reservoir 14 may include a data storage means for storing data that may be interrogated and uploaded at a later time. One of the parameters measured may be reservoir pressure to assist in proper filling and monitoring of the system. For example, if it is found that the reservoir pressure remains constant, one can infer that the compliant body is collapsed or if the pressure is constant for some portion of the cardiac cycle then the balloon is collapsing completely, and needs to be inflated by some volumetric amount until the waveform has no flat sections.

The injection port 16 is structured and operable to allow the addition of gas to or the removal of gas from the reservoir 14. The interior cavity of the injection port 16 is in fluid communication with the reservoir 14 via a lumen of the extravascular conduit 20 such that gas may move freely between the cavities and/or pressure may equalize between the cavities. Optionally, one or more valves may be used to assist with controlling the flow of gas to the reservoir 14. Upon implantation of the pressure reducing device 10, the injection port 16 may be disposed wholly underneath the patient's skin or alternatively may pass through the patient's skin to provide an exposed portion external to the patient's body.

In one exemplary alternative embodiment, the injection port 16 may be mounted directly on the reservoir 14 instead of fluidly coupling the port to the reservoir with the extravascular conduit 20. However, such a design eliminates a surgeon's option of locating the injection port 16 external to the patient's body.

Similar to the compliant body 12 and the reservoir 14, the injection port 16 may be formed from any suitable material or materials that prevent or minimize diffusion of the gas from the internal cavity of the port and through the outer walls. However, the material must be biocompatible such that it is able to perform its function in the body without eliciting an undesirable local or systemic response. The reservoir material is also preferably lubricious and MRI compatible. Radio-opaque or other markers may also be incorporated into or attached to the injection port 16 to allow for viewing or tracking of the injection port with a suitable imaging system.

As illustrated in FIG. 1, the injection port 16 may include a septum 22 that allows for repeated needle penetrations while maintaining a gas-tight seal. Any suitable septum design may be used that provides a gas-tight seal. Exemplary injection ports that may be suitable for use in the pressure reducing device 10 of the invention include the Smart Port®, LifePort®, TitanPort®, Triumph-1®, and Vortex® Ports from AngioDynamicsInc., and the PowerPort®, SlimPort®, X-Port®, and various other M.R.I. compatible ports from C. R. Bard, Inc. The injection port 16 may also be a mechanical structure suitable for direct connection to a syringe for pressure or volume adjustments or a therapeutic gas or liquid supply. The mechanical structure may have internal valves and or electrical contacts.

In embodiments such as that illustrated in FIG. 1 where the injection port 16 is not mounted directly to the reservoir 14 and instead includes the extravascular conduit 20, the conduit is structured for positioning in the subcutaneous space or body cavity adjacent to the reservoir 14 and provides for fluid communication between the components. The extravascular conduit 20 is structured as a thin elongated cylinder with a lumen that allows for conveyance of gas to the reservoir 14. Optionally, the extravascular conduit 20 may include multiple lumens that provide multiple gas lines, or alternatively a first lumen for gas and one or more additional lumens for electrical leads, transmission lines, or the like for transmitting electrical signals between the reservoir 14 and the injection port 16.

The extravascular conduit 20 may be formed from any suitable material or materials that prevent or minimize diffusion of the gas from the lumen or lumens of the conduit. However, the material must be biocompatible such that it is able to perform its function in the body without eliciting an undesirable local or systemic response. The extravascular conduit 20 may be formed from a material that is lubricious, as well as flexible to allow the conduit to move freely within the subcutaneous space or body cavity. The extravascular conduit 20 may also be formed from a material that is MRI-compatible and fatigue resistant such that it maintains its strength and integrity after multiple deformations.

As will be appreciated by those of ordinary skill in the art, it may be important to monitor or track the position of the extravascular conduit 20 after implantation to ensure that the conduit has not moved to an undesirable location. To that end, radio-opaque or other markers may be positioned at discrete intervals along the length of the conduit.

The extravascular conduit 20 may be coupled to the reservoir 14 and the injection port 16 in any suitable manner including, but not limited to, heat welding, a compression fit, or with a biocompatible adhesive.

Finally, the transvascular conduit 18 may be structured as a thin elongated cylinder with a lumen that allows for conveyance of gas and/or equalization of pressure between the reservoir 14 and the compliant body 12. As illustrated in FIG. 1, the proximal end of the transvascular conduit 18 is connected to the reservoir 14. Moving distally away from the reservoir 14, the transvascular conduit 18 starts in the subcutaneous space inferior to the subclavian vein, enters the subclavian vein, passes through the superior vena cava, right atrium, tricuspid valve, right ventricle, and the pulmonary valve, and then enters the pulmonary artery where it connects to the compliant body 12 at its distal end.

As illustrated in FIG. 1, the transvascular conduit 18 may be wholly contained in the lumen of a cardiovascular component. However, in alternative embodiments, the transvascular conduit 18 may pass through the wall of a cardiovascular component such that part of the conduit is in the lumen of a cardiovascular component and part of the conduit is outside the cardiovascular component.

The transvascular conduit 18 may be formed from a biocompatible material that prevents or minimizes diffusion of the gas from the lumen. The transvascular conduit 18 is also preferably flexible so as to allow the conduit to move freely with adjacent body motions such as heart contractions and fatigue resistant such that it maintains its strength and integrity after multiple deformations. In order to impede adhesion of body components and allow for easier insertion through the vasculature, the external surface of the conduit may be lubricious.

Because the transvascular conduit 18 is guided through the patient's vasculature and is therefore not visible by the human eye, it may be desirable to monitor or track the position of the conduit after and/or during implantation. To that end, one or more radio-opaque markers may be incorporated into the wall or positioned at discrete intervals along the length of the transvascular conduit 18 to monitor the location of the conduit and ensure that it is positioned properly within the patient.

The transvascular conduit 18 may be coupled to the compliant body 12 and the reservoir 14 in any suitable manner including, but not limited to, heat welding, a compression fit, or with a biocompatible adhesive. Furthermore, connection of the components may also incorporate the use of one or more valve elements. In one exemplary embodiment, a first two-way valve is positioned at the interface between the compliant body 12 and the distal end of the transvascular conduit 18 and a second two-way valve is positioned at the interface between the reservoir 14 and the proximal end of the transvascular conduit 18.

Optionally, the transvascular conduit 18 may include multiple lumens that provide for multiple gas lines, or alternatively a first lumen for gas and one or more additional lumens for electrical leads, transmission lines, or the like for transmitting electrical signals between the reservoir 14 and the compliant body 12. The transvascular conduit 18 may contain a lumen for a guide wire to assist placement or removal of the device 10. Additionally, the transvascular conduit 18 may include one or more sensors for monitoring physical properties of the cardiovascular system and/or device parameters as discussed above with regard to the other device components. The transvascular conduit may be of varying cross sectional profile and area along its length.

Figure 4:
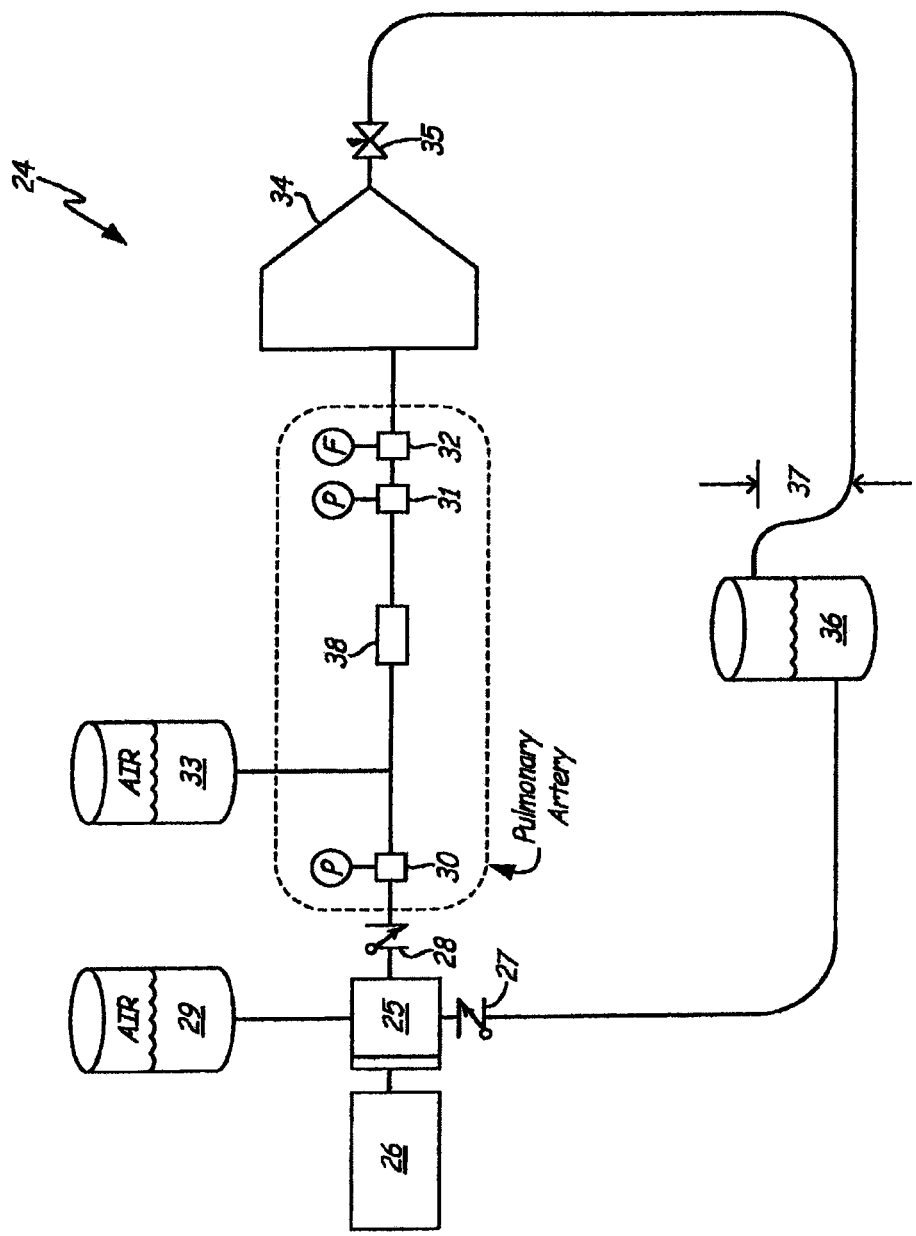
FIG. 4 is a diagram illustrating a "bench top" pulmonary circulation test apparatus used to simulate the operation of the pulmonary vasculature and test various pressure reducing devices in accordance with the invention to verify their operability.

FIG. 4 is a diagram illustrating a "bench top" pulmonary circulation test apparatus 24 used to simulate the operation of the pulmonary vasculature and test various pressure reducing devices in accordance with the invention to verify their operability. As illustrated in FIG. 4, the pulmonary circulation test apparatus 24 is a closed loop circuit that is tuned to match human hemodynamic characteristics of the pulmonary artery. Particularly, the test apparatus 24 includes a chamber 25 operably coupled to a piston pump 26 for simulating the functionality of the right ventricle. The chamber 24 includes a first mechanical valve 27 on an input side simulating the operation of the tricuspid valve and a second mechanical valve 28 on an output side simulating the operation of the pulmonary valve. A first air filled chamber 29 is operably coupled to the chamber for adjusting the "ventricular compliance." The pulmonary artery is simulated in the test apparatus by a first pressure sensor 30, a second pressure sensor 31, a flow meter 32, and a second air filled chamber 33 for adjusting the "arterial compliance." Downstream of the "pulmonary artery components," a bifurcation element 34 and a needle valve 35 simulate the operation of the right and left pulmonary arteries, and a fluid reservoir 36 serves as the source of fluid that is circulated through the test apparatus 24. The fluid reservoir 36 has a capillary wedge pressure 37 that is adjustable.

The particular fluid circulated through the test apparatus was 0.9% saline. Stroke volume, heart rate, mean and pulsatile pressure (mm Hg), flow rate (L/min.), pulmonary vascular resistance (Woods Units), capillary wedge pressure (mm Hg), and compliance of the right ventricle and pulmonary artery were set to match hemodynamic parameters obtained from traces of right heart catheterization procedures from patients with and without pulmonary arterial hypertension. Particularly, the hemodynamic parameters of a typical patient were found to be accurately represented in the test apparatus by a stroke volume of from 30 to 80 ml heart rate of 50 to 100 beats per minute, mean and pulsatile pressure of from 12 to 60 and 10 to 60 mmHg, cardiac output of from 2 to 8 liters per minute, and capillary wedge pressure of from 5 to 20 mmHg.

In order to evaluate the performance of the pressure reducing device of the invention, pressure and flow data were obtained with the device present and absent. When present, the pressure reducing device was operably positioned within the test apparatus 24 at a device location 38 between the first pressure sensor 30 and the second pressure sensor 31.

Figure 5:
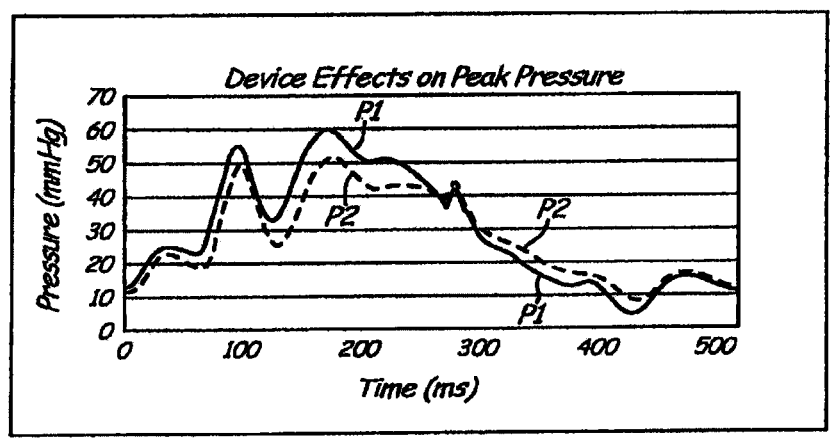
FIG. 5 is a graph illustrating the exemplary effect that the pressure reducing device of the invention has on peak pressure.

FIG. 5 is a graph illustrating the exemplary effect of the pressure reducing device on peak pressure that was achieved using the test apparatus 24. Particularly, the graph tracks changes in pressure during systole and diastole. The first curve P1 represents pressure in a low compliance artery with the device 10 "turned off," while the second curve P2 represents pressure in a low compliance artery with the device 10 "turned on." As illustrated in FIG. 5, the test apparatus demonstrates an approximately 15% reduction in peak pressure when the pressure reducing device is activated. The graph of FIG. 5 also shows how the pressure reducing device causes the pressure to be slightly elevated during diastole, thus having minimal impact on mean pulmonary pressure.

Figure 6A:
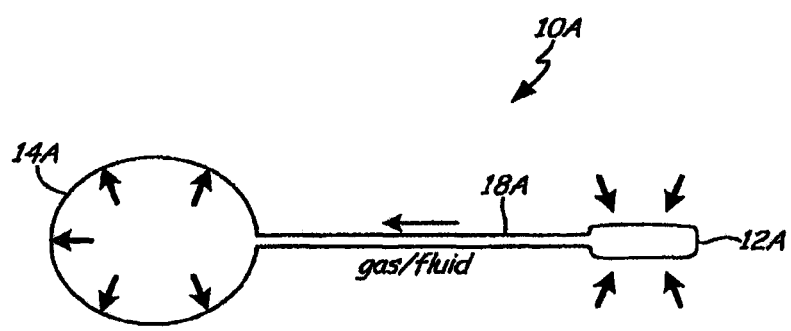
FIGS. 6A and 6B are diagrams illustrating a first alternative embodiment of a pressure reducing device in accordance with the invention.
Figure 6B:
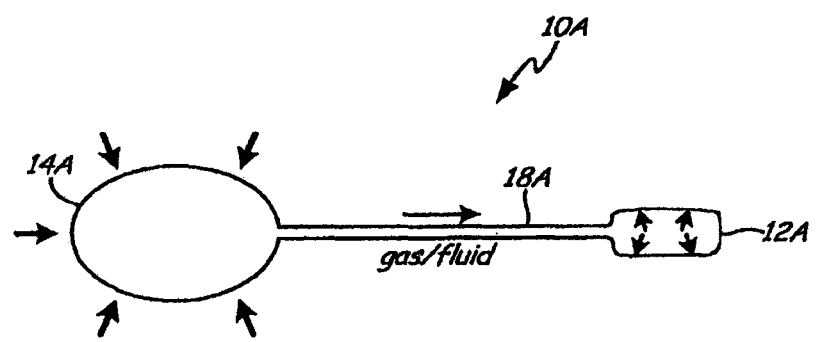

FIGS. 6A and 6B are diagrams illustrating a first alternative embodiment of a pressure reducing device 10 in accordance with the invention. The device 10 is generally similar to the device 10 previously described, and includes a compliant body 12 fluidly coupled to a reservoir 14 by a transvascular conduit 18. Although not illustrated, the device 10 may also include an injection port and an extravascular conduit as previously described. However, unlike the pressure reducing device 10, both the compliant body 12 and the reservoir 14 of the device 10 are formed from an elastic material. Additionally, the device 10 may be filled with either a compressible gas (as discussed in detail above) or a non-compressible fluid (of any state). As will be appreciated by those of ordinary skill in the art, any fluid that is both non-compressible and biocompatible may be used, such as a saline solution.

As illustrated in FIG. 6A, during systole ($P_{PulmonaryArtery} > P_{Reservoir}$), high pressure in the pulmonary artery causes the gas/fluid to move out of the compliant body 12 and into the reservoir 14. The elasticity of the reservoir walls allows the reservoir 14 to stretch and accommodate an increased volume. Conversely, during diastole ($P_{PulmonaryArtery} < P_{Reservoir}$), the elastic forces of the walls of the reservoir 14 move the gas/fluid back into the compliant body 12 as illustrated in FIG. 6B, thus increasing the volume of the compliant body 12. As will be appreciated by those of ordinary skill in the art, the net effect of the movement of gas/fluid between the compliant body 12 and the reservoir 14 is to reduce systolic pressure and boost diastolic pressure in the pulmonary artery. In this embodiment, the compliance in the pulmonary artery is increased during systole primarily by stretching of the reservoir's elastic walls rather than compression of the gas in the compliant body.

One benefit of using a non-compressible fluid in place of a compressible gas may be less need for refilling the device 10 after implantation. Additionally, a non-compressible fluid may allow for better control when used in an active system as will be described below with reference to FIG. 7. Numerous other benefits are inherent to the use of a non-compressible fluid as will be appreciated by those of ordinary skill in the art.

Figure 7:
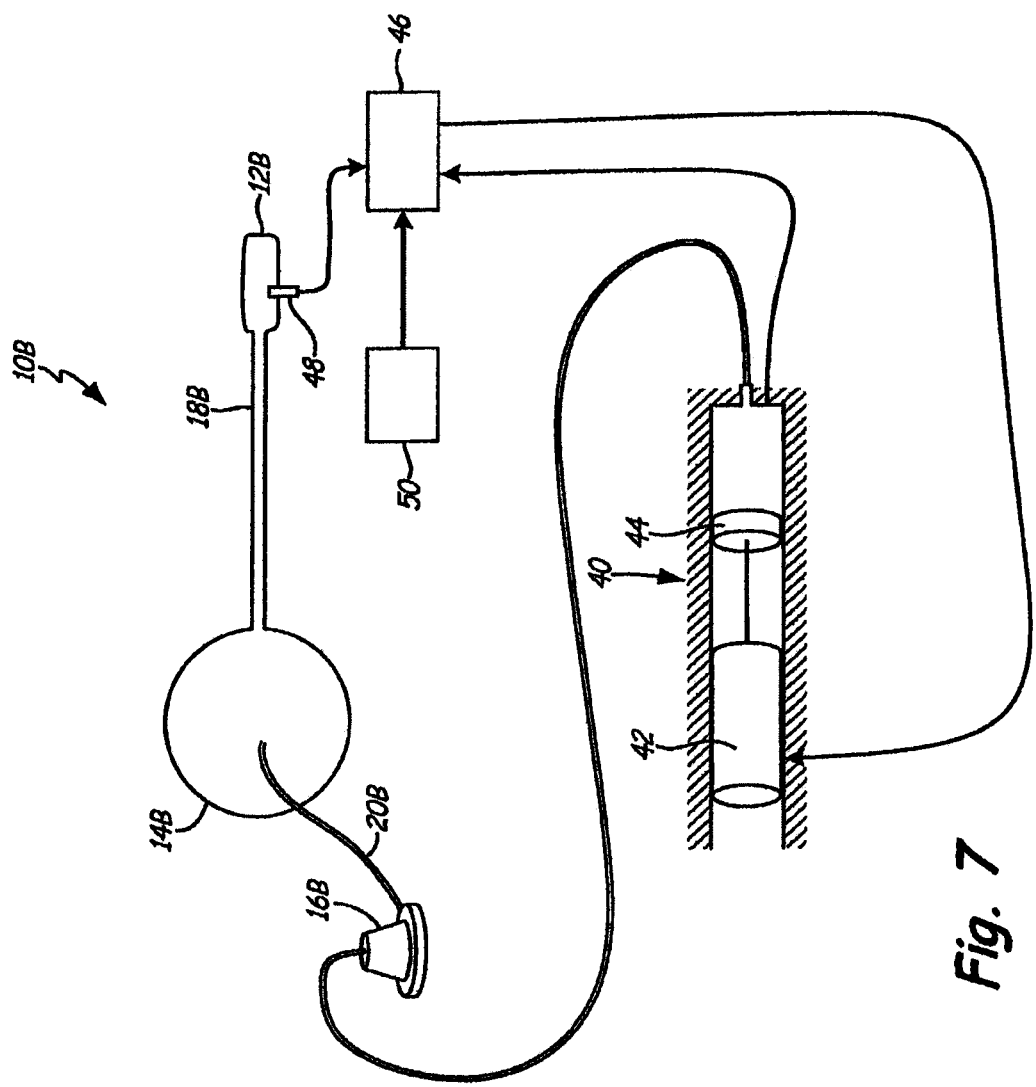
FIG. 7 is a diagram illustrating a second alternative embodiment of a pressure reducing device in accordance with the invention.

FIG. 7 is a diagram illustrating a second alternative embodiment of a pressure reducing device 10B in accordance with the invention. The device 10B may be generally similar to either the device 10 or the device 10A previously described, and includes a compliant body 12B, a reservoir 14B, an injection port 16B, a transvascular conduit 18B fluidly coupling the compliant body 12B to the reservoir 14B, and an extravascular conduit 20B fluidly coupling the reservoir 14B to the injection port 16B. However, as illustrated in FIG. 7, the pressure reducing device 10B further includes a controllable pulsatile pump 40 that allows for active control of the inflation/deflation of the compliant body 12B. Any suitable pump that is operable to control the movement of fluid within the pressure reducing device 10B may be used as those of ordinary skill in the art will appreciate. In one exemplary embodiment as illustrated in FIG. 7, the pulsatile pump 40 may include a linear actuator 42 that is operable to precisely control the linear movement of a piston 44 to inject fluid into and extract fluid from the compliant body 12B.

Particularly, the device 10 may function as an open or closed loop control system that is operable to minimize cardiac work while maintaining cardiac output. In one exemplary embodiment, the device 10 may be operable to increase compliance in the pulmonary artery by decreasing the volume in the compliant body 12 during systole and increasing the volume in the compliant body 12 during diastole. As will be appreciated by those of ordinary skill in the art, the overall effect is to decrease systolic pressure and increase the pressure during diastole and between beats.

The pulsatile pump 40 may be a permanent part of the device 10, or it may be operably coupled to the device 10 for short-term use. This would allow the pressure reducing device 10 to adapt to patient needs by adding the functionality of an active system whenever necessary, such as for emergency therapy or as the disease progresses.

A suitable control means such as a CPU 46 may be operably coupled to the pulsatile pump 40 for controlling operation of the pump. The CPU 46 may receive input signals from one or more sensors or monitoring devices, such as a pressure sensor 48 operably coupled to the compliant body 12 and an ECG 50 operably coupled to the patient. However, sensors may be provided that monitor numerous other types of parameters or properties. Additionally, the CPU 46 may be operably coupled to an input means to allow for the manual input of control commands by the attending physician.

The foregoing alternative embodiments were described merely for purposes of example and not limitation. As will be appreciated by those of ordinary skill in the art, the pressure reducing devices of the invention may be provided with numerous other design features and functionalities. In another alternative embodiment, the pressure reducing device may include a lumen for delivering one or more drugs to a patient. The drugs may work together with the pressure reducing device to relieve the effects of pulmonary arterial hypertension. In another alternative embodiment, the transvascular conduit may carry one or more electrical leads for a pacemaker device that helps control abnormal heart rhythms. Alternatively, the conduit itself may contain electrical conduction properties so that it may function as a lead for a pacemaker. The pacemaker device that is operably coupled to the leads may be incorporated into the pressure reducing device of the invention, such as being attached to or positioned within the reservoir. Alternatively, the pacemaker device may be a stand-alone unit that is implanted separately from the reservoir. In yet another alternative embodiment, the pressure reducing device of the invention may include a pressure relief means for relieving the buildup of pressure within the device to prevent damage to the device and/or physical harm to the patient. For example, the pressure relief means may comprise a pressure relief valve associated with one or more components of the device, such as the reservoir, that is designed to open at a predetermined set pressure to protect the device from being subjected to pressures that exceed its design limits.

As will be appreciated by those of ordinary skill in the art based on the foregoing, the invention provides numerous benefits and advantages over previous designs. The pressure reducing device of the invention may be implanted in a minimally invasive procedure that does not require general anesthesia. This is an important factor for patients with advanced cardio respiratory compromise, as occurs with pulmonary arterial hypertension. Furthermore, the implantation procedure may be performed by a physician with minimal surgical skill such as an interventional radiologist, interventional cardiologist, or a cardiologist. Not only is the device of the invention easily implantable, but it is also removable.

In one embodiment, the pressure reducing device of the invention may be passive and therefore would not require an external energy source. It would also address the problem of filling the device upon initial implantation and keeping the device inflated over time. Particularly, the device provides remote access via the injection port which allows the compliant body to be queried and adjusted to a desired inflation level. Thus, the device does not require a transvascular procedure to fill and does not require an access line to cross an arterial wall.

Although passive devices are simpler and well-suited for long term use, active embodiments, as disclosed herein, are also contemplated and within the scope of the invention. Active device are suited for situations that require more control, such as for emergency therapy or when the disease progresses.

The long compliant body of the pressure reducing device is designed to slow the PWV (i.e. minimize the effect of reflected waves on pulse pressure). Particularly, the long, thin shape of the compliant body minimizes the cross-sectional area of the artery that is taken up by the device. Consequently, the resistance to flow caused by the presence of the compliant body in the artery is minimized (i.e. minimal intra-arterial volume means minimum flow restriction caused by the device).

As will be appreciated by those of ordinary skill in the art, providing a long, thin compliant body in combination with a large extravascular reservoir located remote from the pulmonary artery increases vascular compliance due to the fact that much of the fluid volume is located outside of the artery. As will further be appreciated by those of ordinary skill in the art, a large reservoir volume translates to better performance with respect to pressure reduction.

Another benefit of the invention is the capability of monitoring one or more physical properties of the cardiovascular system and/or one or more parameters of the pressure reducing device. The monitoring may be performed using any suitable sensor operably coupled to the reservoir, compliant body, injection port, extravascular conduit, or transvascular conduit. The monitored properties or parameters may include temperature, pressure, flow rate, oxygenation, $CO_2$ concentration, pH, luminal diameter, or the like.

In addition to providing components that assist with the reduction of pressure within the cardiovascular system, the device of the invention may also include components that assist with the delivery of one or more drugs. In one exemplary embodiment, the device may be operable to deliver a drug for treating pulmonary arterial hypertension, such as Iloprost.

Figure 8:
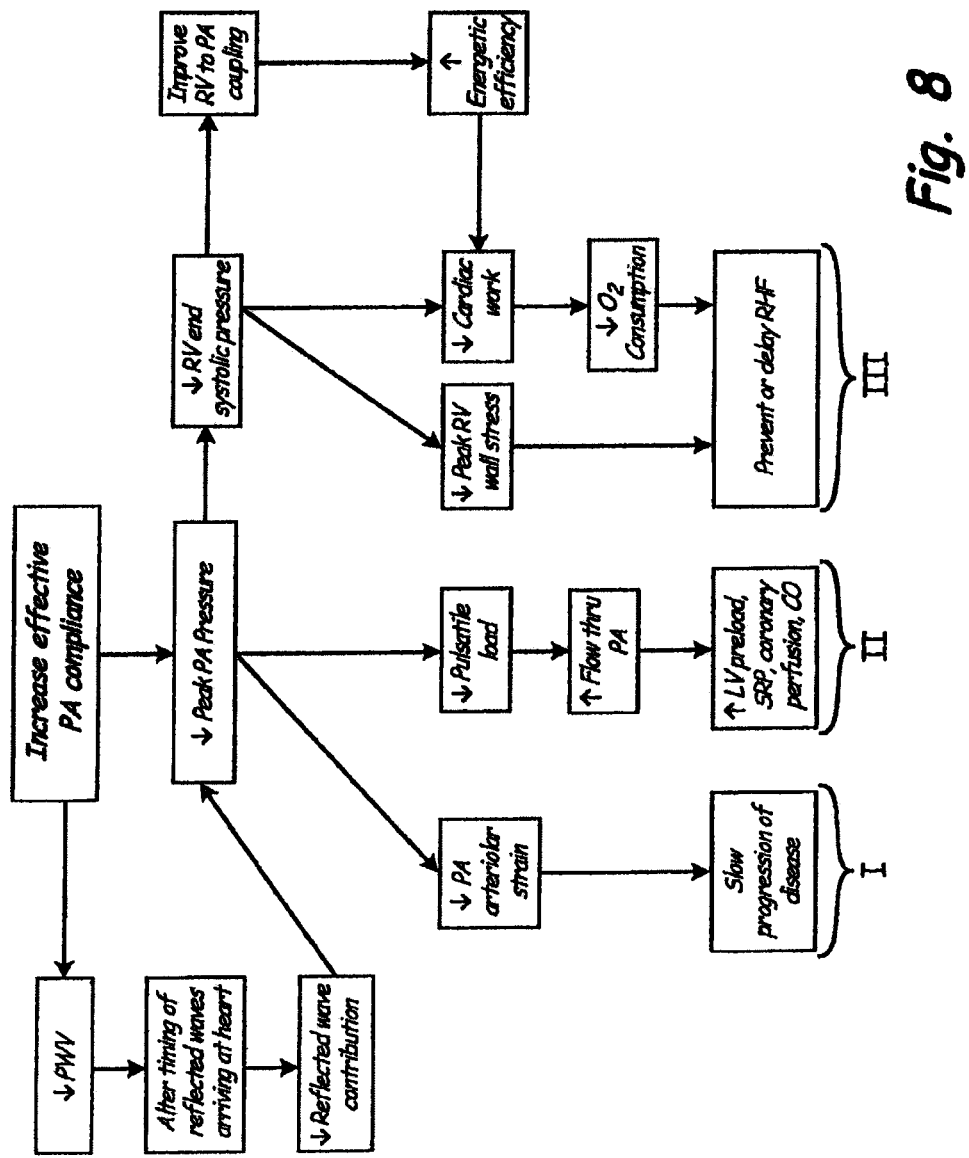
FIG. 8 is a flowchart diagram illustrating exemplary but non-limiting therapeutic pathways associated with the pressure reducing device of the invention.

FIG. 8 is a flowchart diagram illustrating exemplary but non-limiting therapeutic pathways associated with the pressure reducing device of the invention. In summary, by increasing the compliance of the pulmonary artery the device of the invention is able to (I) slow the progression of small vessel disease, (II) increase cardiac output, and (III) prevent or delay the onset of right heart failure.

Although the invention has been described with reference to preferred embodiments, workers skilled in the art will recognize that changes may be made in form and detail without departing from the spirit and scope of the invention.

What is claimed is:

1. Apparatus for improving compliance of a pulmonary artery, the apparatus comprising: a subcutaneously implantable reservoir configured to hold a fluid; a conduit having first and second implantable ends, the first implantable end configured to be coupled to the subcutaneously implantable reservoir to provide fluidic communication between the subcutaneously implantable reservoir and the conduit; and a compliant body configured to be fully implantable, the compliant body coupled to the second implantable end of the conduit to provide fluidic communication between the compliant body and the conduit, the compliant body configured to be implanted in the pulmonary artery; and a fluid disposed in the subcutaneously implantable reservoir, conduit, and compliant body, the fluid pressurized such that the compliant body transitions between an expanded state and a contracted state responsive to pressure change in the pulmonary artery, wherein a distal end of the compliant body comprises a T shape configured to form arms that extend into branches of the pulmonary artery, distal to bifurcation of the pulmonary artery, and wherein the compliant body is configured to transition to the contracted state during systole to move fluid towards the reservoir and to transition to the expanded state during diastole.

2. The apparatus of claim 1, further comprising an injection port coupled to the subcutaneously implantable reservoir, the injection port configured to permit fluid filling and pressure adjustments.

3. The apparatus of claim 2, wherein the injection port is mounted directly on the subcutaneously implantable reservoir.

4. The apparatus of claim 1, further comprising an anchoring member configured to anchor the compliant body in the pulmonary artery.

5. The apparatus of claim 4, wherein the anchoring system is configured to be anchored in the pulmonary artery distal to bifurcation of the pulmonary artery.

6. The apparatus of claim 4, wherein the anchoring system comprises a wire removably coupled to the compliant body.

7. The apparatus of claim 6, wherein the wire is configured to be inserted through a lumen in the conduit.

8. The apparatus of claim 1, further comprising a sheath having a sheath lumen therethrough, the compliant body and the conduit configured to be introduced through the sheath lumen.

9. The apparatus of claim 8, further comprising an anchoring member coupled to the sheath, the anchoring member configured to anchor the sheath in the pulmonary artery.

10. The apparatus of claim 1, wherein the conduit comprises two lumens extending between the compliant body and the subcutaneously implantable reservoir.

11. The apparatus of claim 10, further comprising a one-way valve disposed in one of the two lumens, the one-way valve configured to permit the fluid to flow to the compliant body through one lumen and return from the compliant body through another lumen.

12. The apparatus of claim 1, wherein the fluid is compressible.

13. The apparatus of claim 1, wherein the fluid comprises a gas.

14. The apparatus of claim 1, further comprising a sensor configured to monitor at least one of fluid pressure or volume.

15. The apparatus of claim 14, wherein the sensor is disposed within the subcutaneously implantable reservoir.

16. The apparatus of claim 1, wherein the compliant body comprises a material configured to reduce diffusion of the fluid from the compliant body.

17. A method for improving compliance of a pulmonary artery, the method comprising: implanting a compliant body within a pulmonary artery, the compliant body configured to be coupled to a conduit and fluidly coupled to a reservoir configured to hold a fluid, the fluid pressurized such that the compliant body transitions between an expanded stated and a contracted state responsive to pressure change in the pulmonary artery, wherein a distal end of the compliant body has a T shape configured to form arms that extend into branches of the pulmonary artery, distal to bifurcation of the pulmonary artery; contracting the compliant body to the contracted state responsive to a pressure change in the pulmonary artery during systole to move the fluid towards the reservoir; and expanding the compliant body to the expanded state responsive to a pressure change in the pulmonary artery during diastole.

18. The method of claim 17, further comprising anchoring the compliant body within the pulmonary artery using an anchoring member.

19. The method of claim 17, wherein implanting the compliant body comprises implanting the compliant body through a sheath.

20. The method of claim 17, further comprising filling the reservoir with the fluid via an injection port attached to the reservoir.

21. Apparatus for improving compliance of a pulmonary artery, the apparatus comprising: a reservoir configured to hold a fluid; a conduit in fluidic communication with the reservoir; a balloon in fluidic communication with the conduit and the reservoir, the balloon configured to be implanted in the pulmonary artery, wherein the fluid is pressurized such that the balloon transitions between an expanded state and a contracted state responsive to pressure change in the pulmonary artery; and an anchor configured to anchor the balloon in the pulmonary artery, the anchor comprising wire configured to be disposed in a lumen in the conduit.

22. The apparatus of claim 21, where the transitions of the balloon between the expanded state and the contracted state treat pulmonary hypertension.

23. The apparatus of claim 21, wherein the balloon comprises a Y or T shape configured to form arms that extend into branches of the pulmonary artery, distal to bifurcation of the pulmonary artery.

24. The apparatus of claim 21, wherein the balloon is configured to transition to the contracted state during systole to move the fluid towards the reservoir and to transition to the expanded state during diastole.

25. The apparatus of claim 21, further comprising an injection port coupled to the reservoir, the injection port configured to permit fluid filling and pressure adjustments.

26. The apparatus of claim 25, wherein the injection port is mounted directly on the reservoir and the reservoir is configured to be implanted subcutaneously.

27. The apparatus of claim 21, wherein the anchor is disposed distal to the balloon in the pulmonary artery.

28. The apparatus of claim 21, wherein the anchor is configured to be anchored in the pulmonary artery distal to bifurcation of the pulmonary artery.

29. The apparatus of claim 21, wherein the anchor is configured to extend out a distal end of the conduit.

30. The apparatus of claim 21, wherein the wire comprises members configured to be compressed in a sheath and configured to expand to contact an inner wall of the pulmonary artery upon removal of the sheath.

31. The apparatus of claim 21, wherein the conduit and the balloon are moveable along the wire.

32. The apparatus of claim 21, wherein the anchor is configured to expand outwardly upon deployment to contact an inner wall of the pulmonary artery.

33. The apparatus of claim 21, wherein the conduit is configured to be pulled proximally to remove the balloon from the pulmonary artery.

34. The apparatus of claim 21, further comprising a sheath having a sheath lumen, the balloon and the conduit configured to be introduced through the sheath lumen.

35. The apparatus of claim 21, wherein the fluid comprises a gas.

36. The apparatus of claim 35, wherein the gas comprises nitrogen or carbon dioxide or both.

37. The apparatus of claim 21, wherein the fluid is compressible.

38. A method for improving compliance of a pulmonary artery, the method comprising: anchoring a balloon within a pulmonary artery using an anchor, the balloon configured to be coupled to a conduit and fluidly coupled to a reservoir configured to hold a fluid, the fluid pressurized such that the balloon transitions between an expanded stated and a contracted state responsive to pressure change in the pulmonary artery, the anchor comprising wire configured to be disposed in a lumen in the conduit; contracting the balloon to the contracted state responsive to a pressure change in the pulmonary artery during systole to move the fluid towards the reservoir; and expanding the balloon to the expanded state responsive to a pressure change in the pulmonary artery during diastole.

39. The method of claim 38, wherein the contracting and the expanding the balloon treat pulmonary hypertension.

40. The method of claim 38, wherein anchoring the balloon within the pulmonary artery using the anchor comprises outwardly expanding the anchor upon deployment to contact an inner wall of the pulmonary artery.

41. The method of claim 38, wherein anchoring the balloon comprises implanting the balloon through a sheath.

42. The method of claim 38, further comprising filling the reservoir with the fluid via an injection port attached to the reservoir.

\* \* \* \* \*